US010174355B2

(12) United States Patent
Kim et al.

(10) Patent No.: US 10,174,355 B2
(45) Date of Patent: Jan. 8, 2019

(54) METHOD FOR GLYCOSYLATION OF GINSENOSIDE USING A GLYCOSYLTRANSFERASE DERIVED FROM PANAX GINSENG

(71) Applicants: KOREA ADVANCED INSTITUTE OF SCIENCE AND TECHNOLOGY, Daejeon (KR); INTELLIGENT SYNTHETIC BIOLOGY CENTER, Daejeon (KR)

(72) Inventors: Sun Chang Kim, Daejeon (KR); Gil Tsu Choi, Daejeon (KR); Suk Chae Jung, Daejeon (KR); Myung Keun Park, Daejeon (KR); Woo Hyun Kim, Daejeon (KR); Soo Hwan Lim, Daejeon (KR); Wan Taek Im, Daejeon (KR)

(73) Assignees: Korea Advanced Institute of Science and Technology (KR); Intelligent Synthetic Biology Center (KR)

( * ) Notice: Subject to any disclaimer, the term of this patent is extended or adjusted under 35 U.S.C. 154(b) by 0 days.

(21) Appl. No.: 15/307,582

(22) PCT Filed: Apr. 30, 2015

(86) PCT No.: PCT/KR2015/004399
§ 371 (c)(1),
(2) Date: Oct. 28, 2016

(87) PCT Pub. No.: WO2015/167282
PCT Pub. Date: Nov. 5, 2015

(65) Prior Publication Data
US 2017/0121750 A1    May 4, 2017

(30) Foreign Application Priority Data

Apr. 30, 2014  (KR) .................. 10-2014-0052728

(51) Int. Cl.
*C12P 33/00* (2006.01)
*C12N 9/10* (2006.01)
*C12P 33/20* (2006.01)

(52) U.S. Cl.
CPC .............. *C12P 33/00* (2013.01); *C12N 9/10* (2013.01); *C12N 9/1051* (2013.01); *C12P 33/20* (2013.01); *C12Y 204/01017* (2013.01)

(58) Field of Classification Search
None
See application file for complete search history.

(56) References Cited

FOREIGN PATENT DOCUMENTS

| WO | 2014/051214 A1 | 4/2014 |
|---|---|---|
| WO | 2014/051215 A1 | 4/2014 |
| WO | 2014/086317 A1 | 6/2014 |

OTHER PUBLICATIONS

Office Action, Application No. 2016-565151, Japanese Patent Office, dated Nov. 7, 2017.
Dai et al., "Metabolic engineering of *Saccharomyces cerevisiae* for production of ginsenosides", Metabolic Engineering, Nov. 2013, vol. 20, pp. 145-156.
Yan et al., "Production of bioactive ginsenoside compound K in metabolically engineered yeast", Cell Research, Mar. 7, 2014, vol. 24, pp. 770-773.
Yan et al., "Panax ginseng UGT1 mRNA, complete cds", GenBank [online], Accession No. KF377585, Jul. 5, 2014, retrieval date: Oct. 31, 2017.

*Primary Examiner* — Richard G Hutson
(74) *Attorney, Agent, or Firm* — Gavrilovich, Dodd & Lindsey LLP

(57) ABSTRACT

The present invention relates to a uridine diphosphate (UDP)-glycosyltransferase protein which has glycosylation activity for a hydroxyl group at the C-20 position of a protopanaxadiol (PPD)- or protopanaxatriol (PPT)-type ginsenoside, and a method for glycosylation of UDP using the same.

3 Claims, 13 Drawing Sheets

Specification includes a Sequence Listing.

[Fig. 1]

| Ginsenosides | R₁ | R₂ |
|---|---|---|
| Rb₁ | Glc²-Glc | Glc⁶-Glc |
| Rd | Glc²-Glc | Glc |
| F2 | Glc | Glc |
| Rg₃ | Glc²-Glc | H |
| Rh₂ | Glc | H |
| Compound K | H | Glc |
| PPD | H | H |
| Rb₂ | Glc²-Glc | Glc⁶-Ara(p) |
| Rc | Glc²-Glc | Glc⁶-Ara(f) |
| Compound MC | H | Glc⁶-Ara(f) |
| Compound Y | H | Glc⁶-Ara(p) |

| Ginsenosides | R₁ | R₂ |
|---|---|---|
| Rg₁ | Glc | Glc |
| Rh₁ | Glc | H |
| F1 | H | Glc |
| Rf | Glc²-Glc | H |
| PPT | H | H |
| Re | Glc²-Rha | Glc |
| Rg₂ | Glc²-Rha | H |

[Fig. 2]
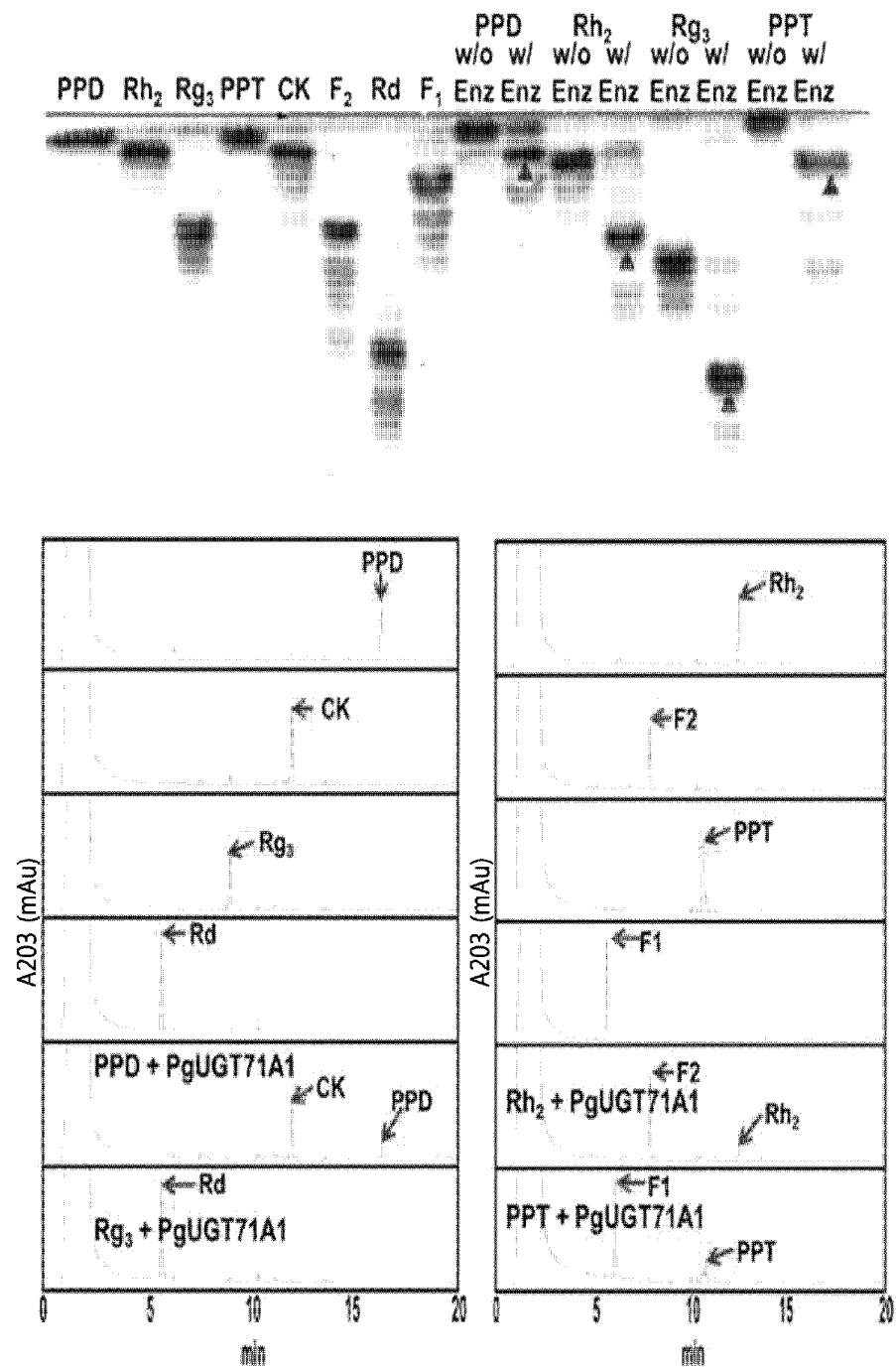

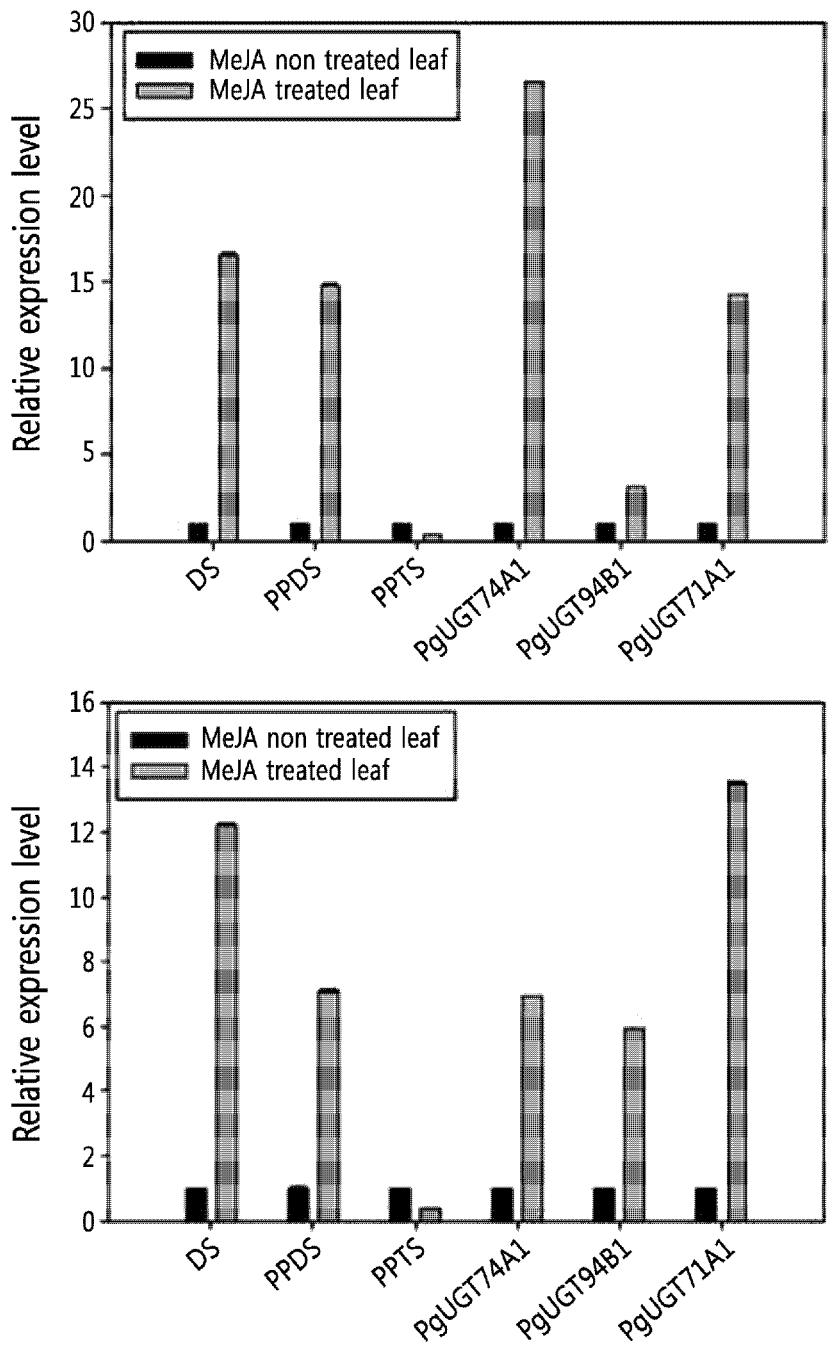
[Fig. 3]

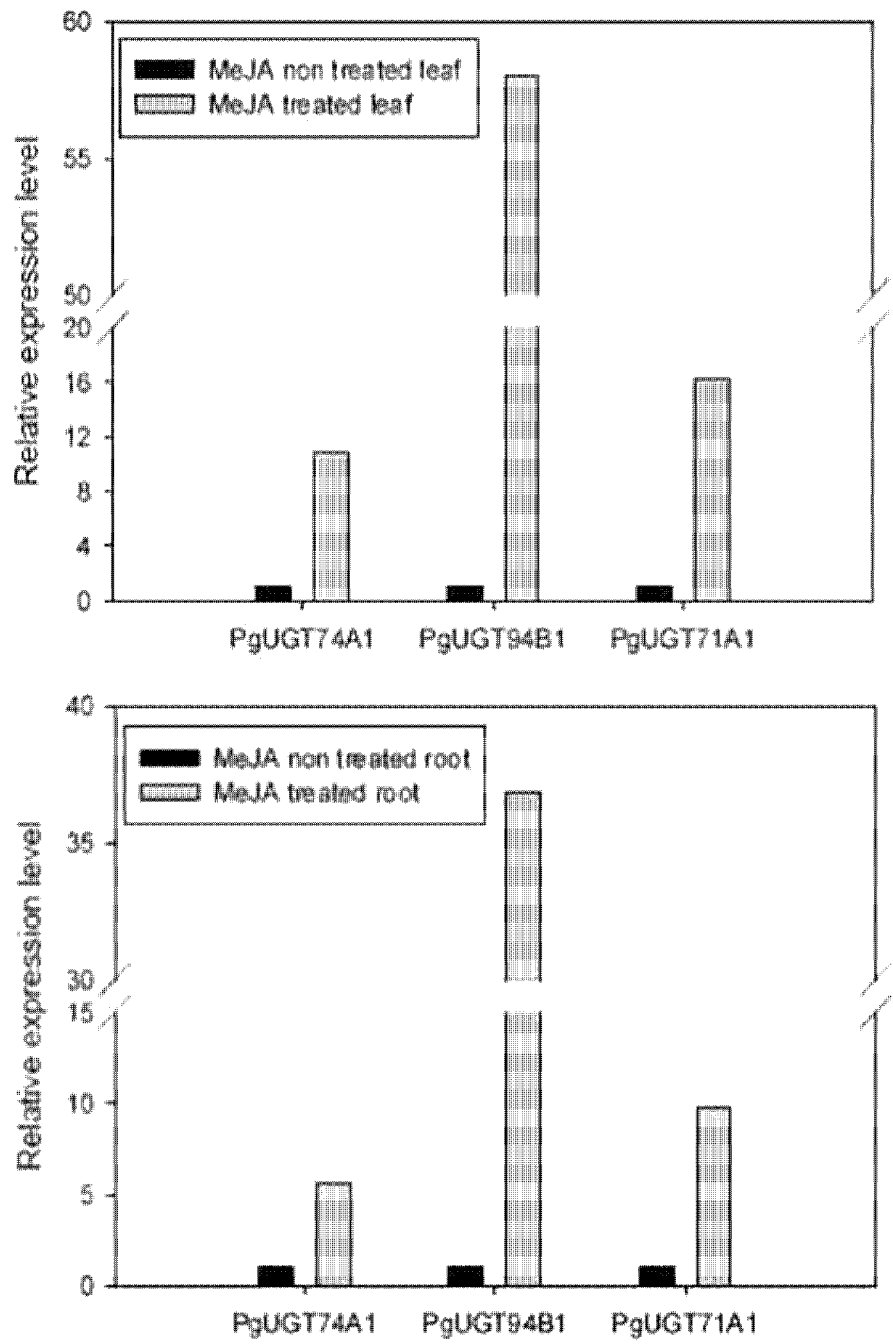
[Fig. 4]

[Fig. 5]
(A)
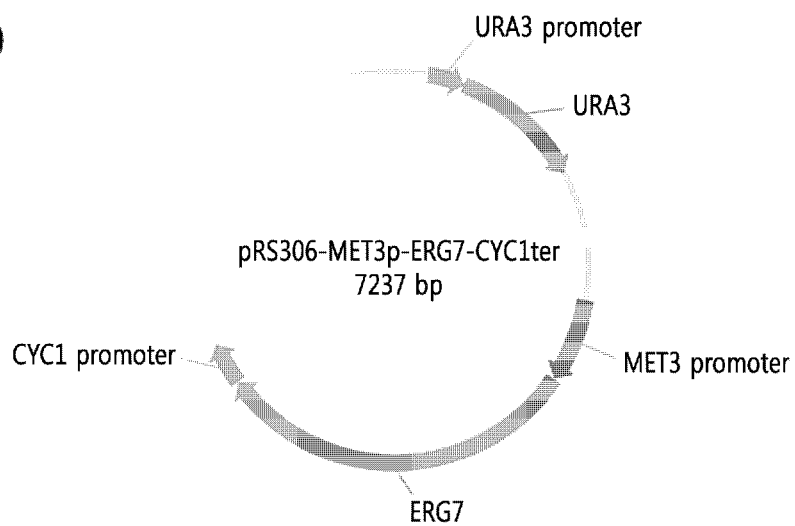
(B) ERG7 down regulation cassette
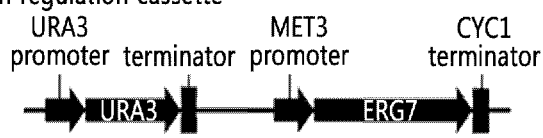
Homologous recombination
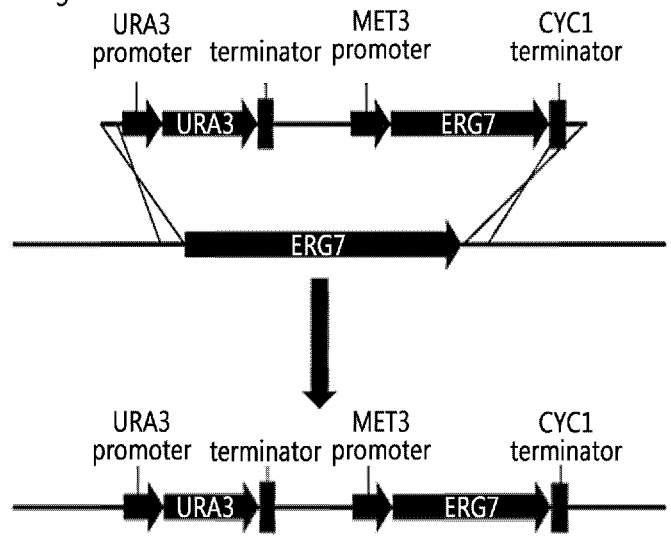

[Fig. 6]
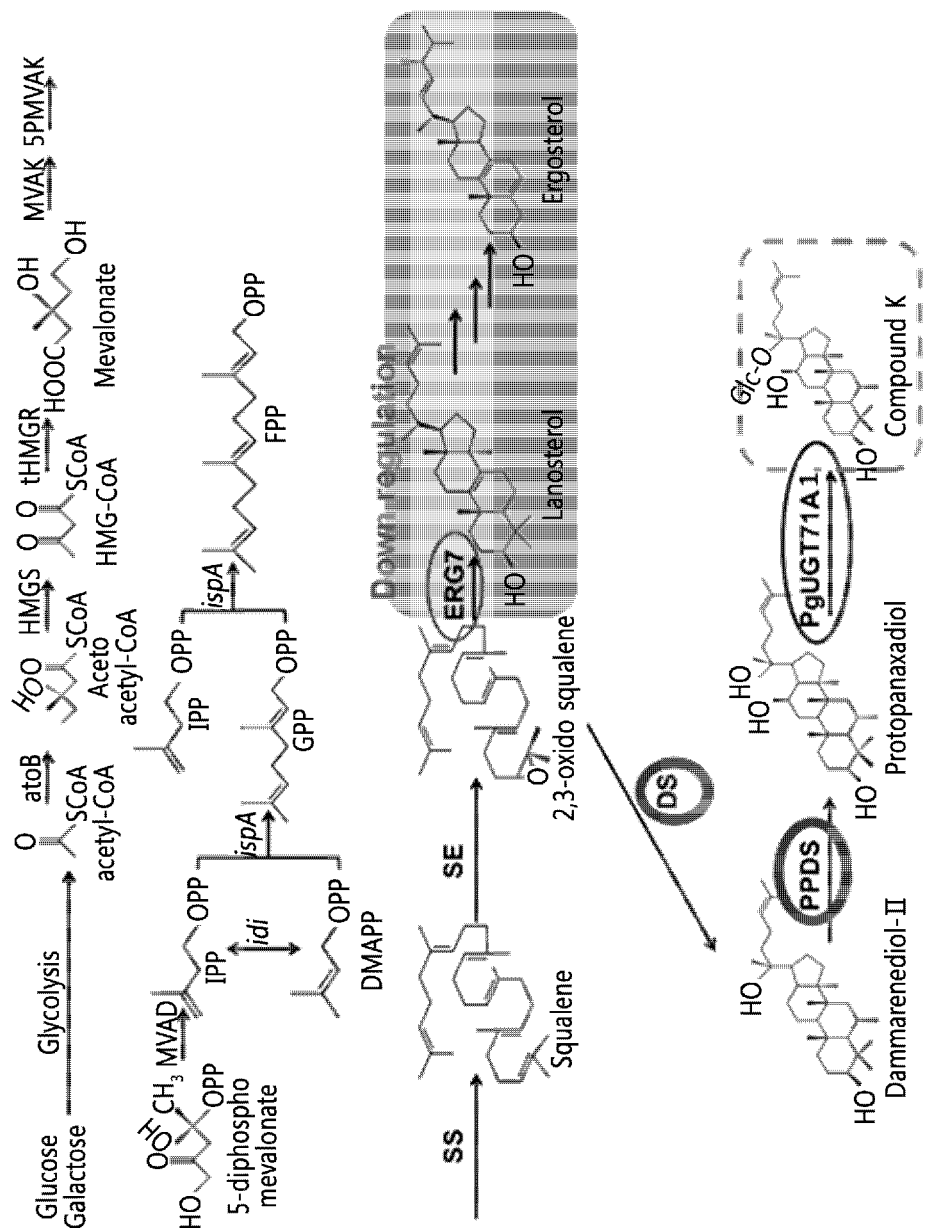

[Fig. 7]
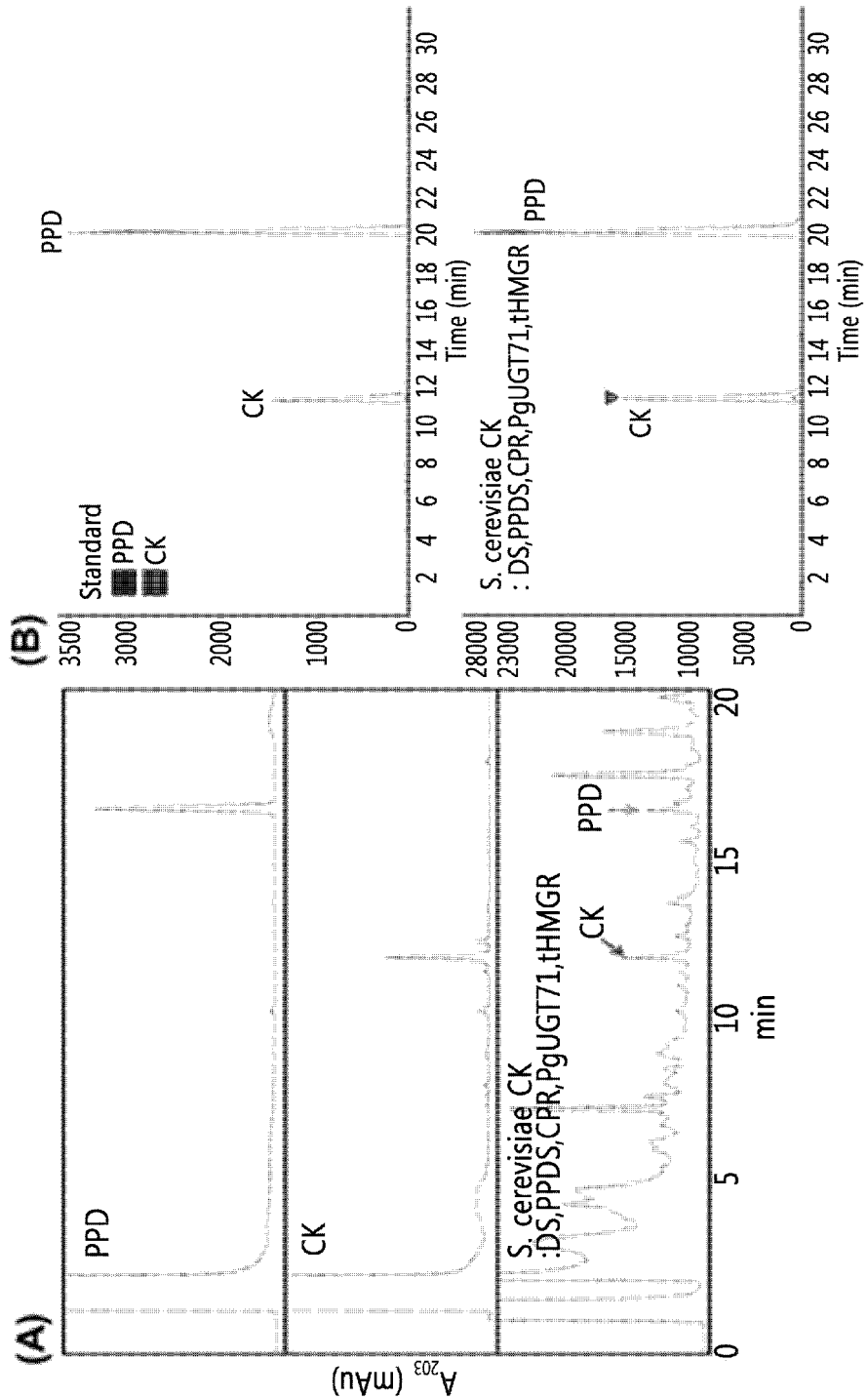

[Fig. 8]
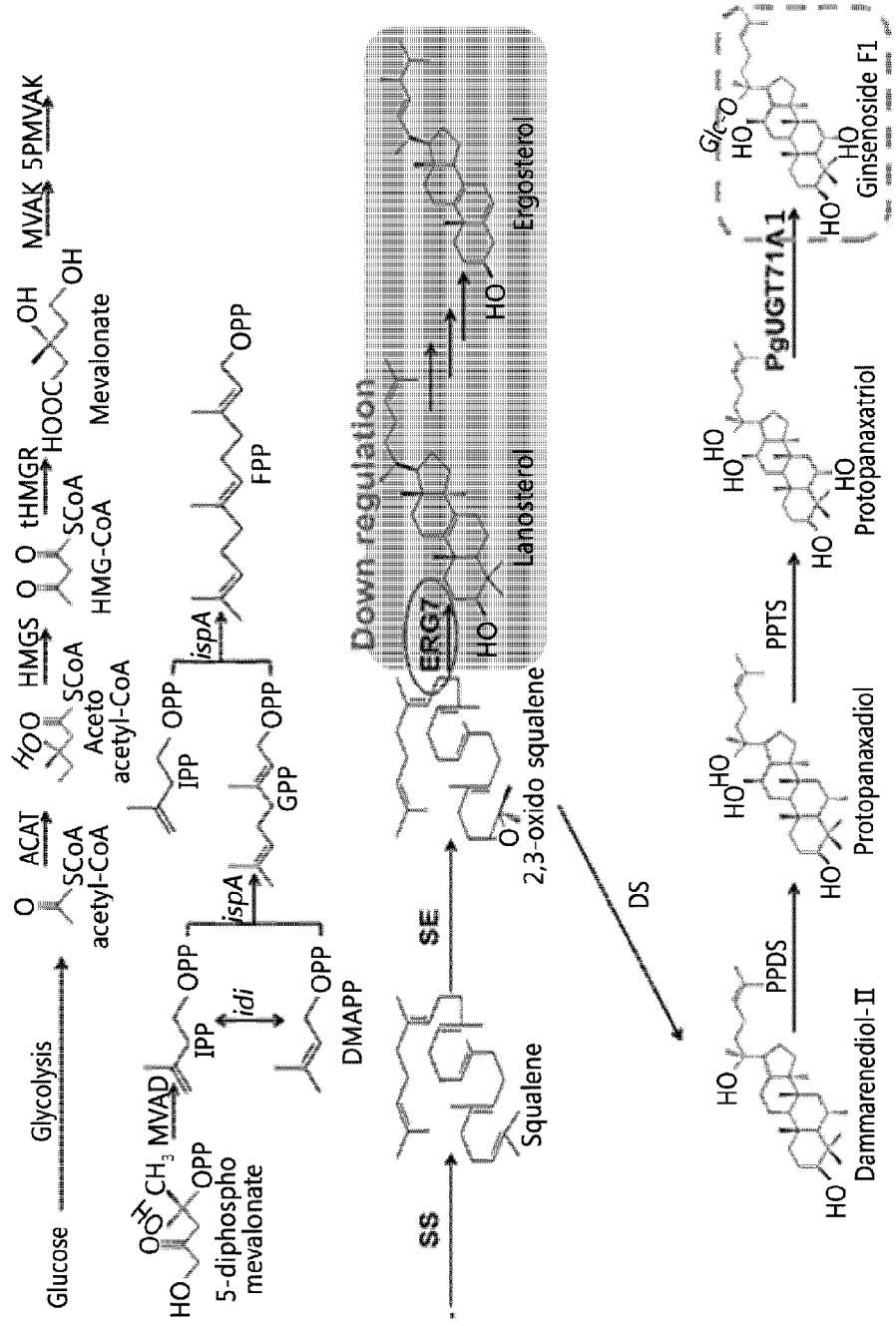

[Fig. 9]
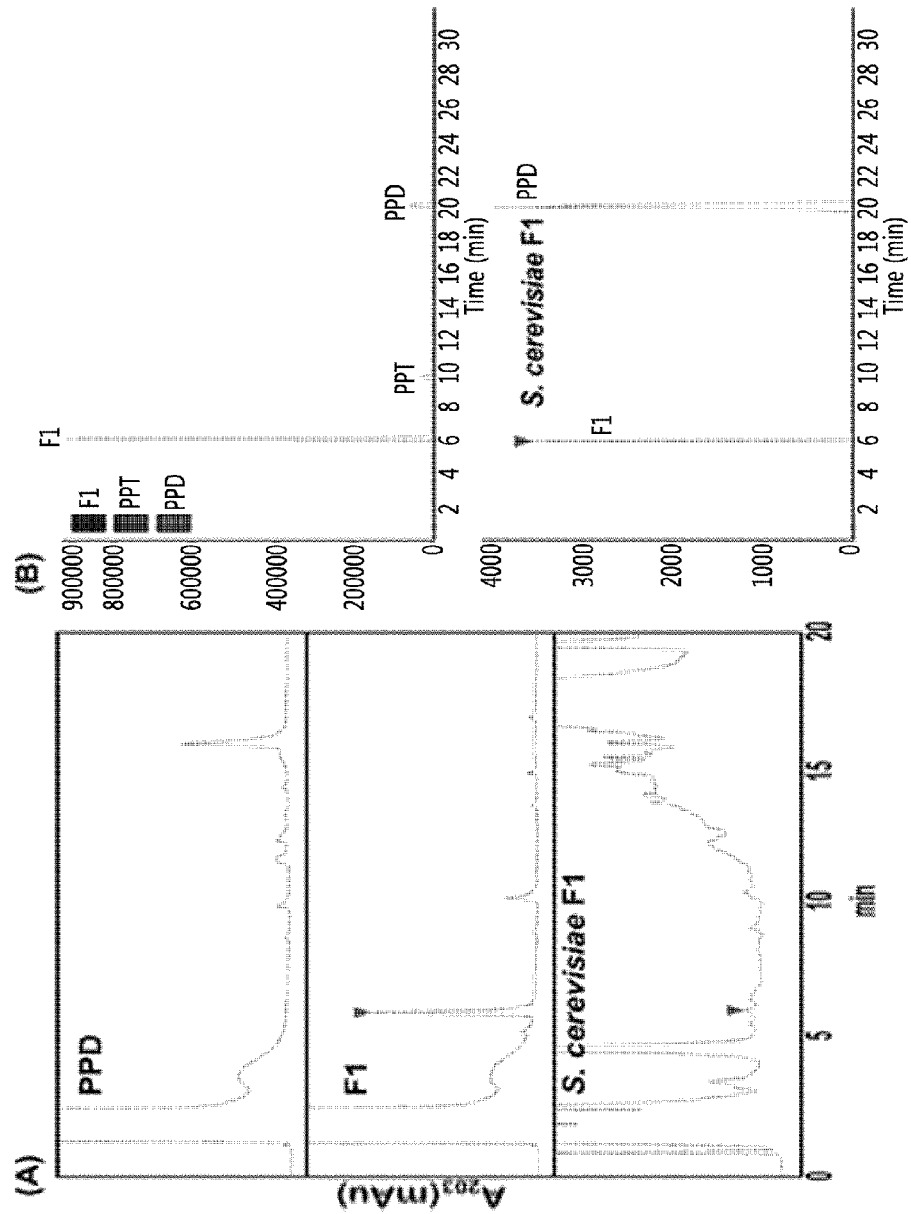

[Fig. 10]
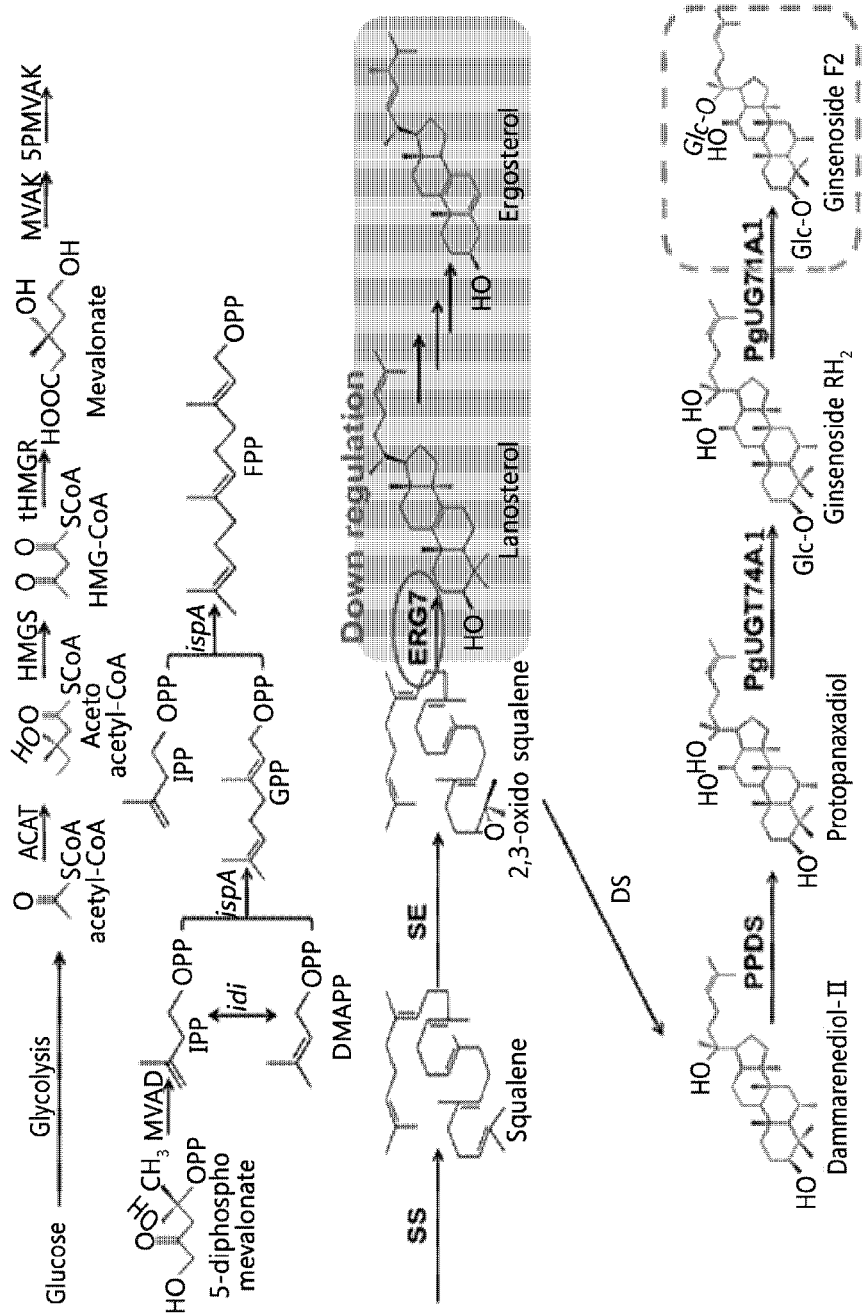

[Fig. 11]
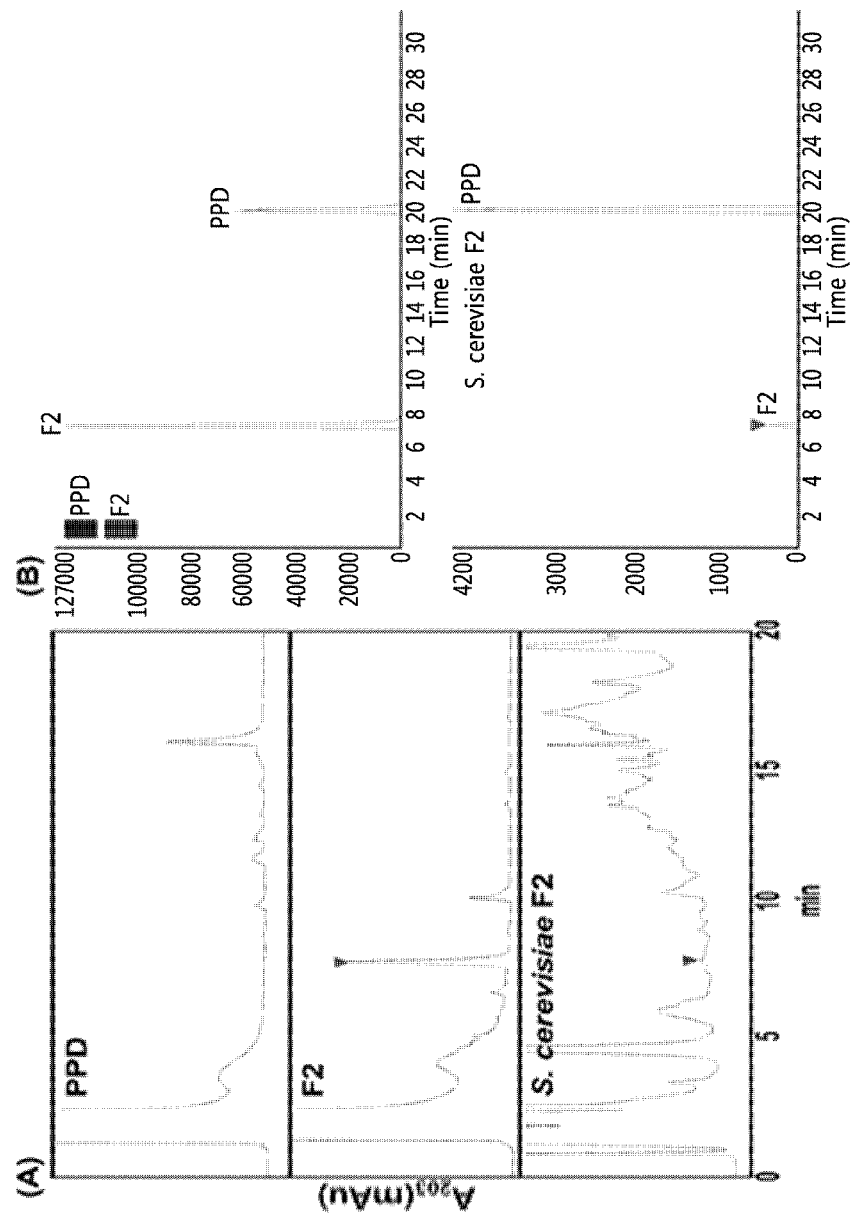

[Fig. 12]
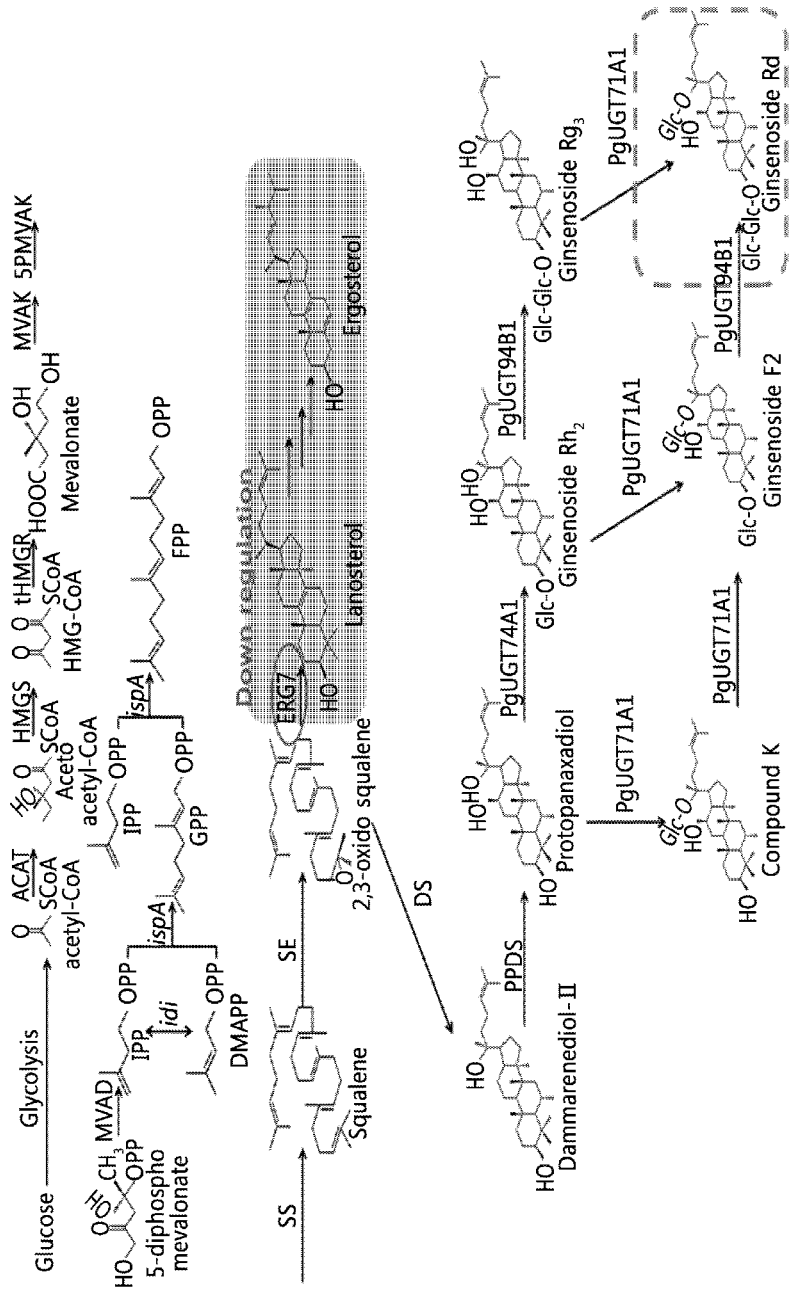

[Fig. 13]
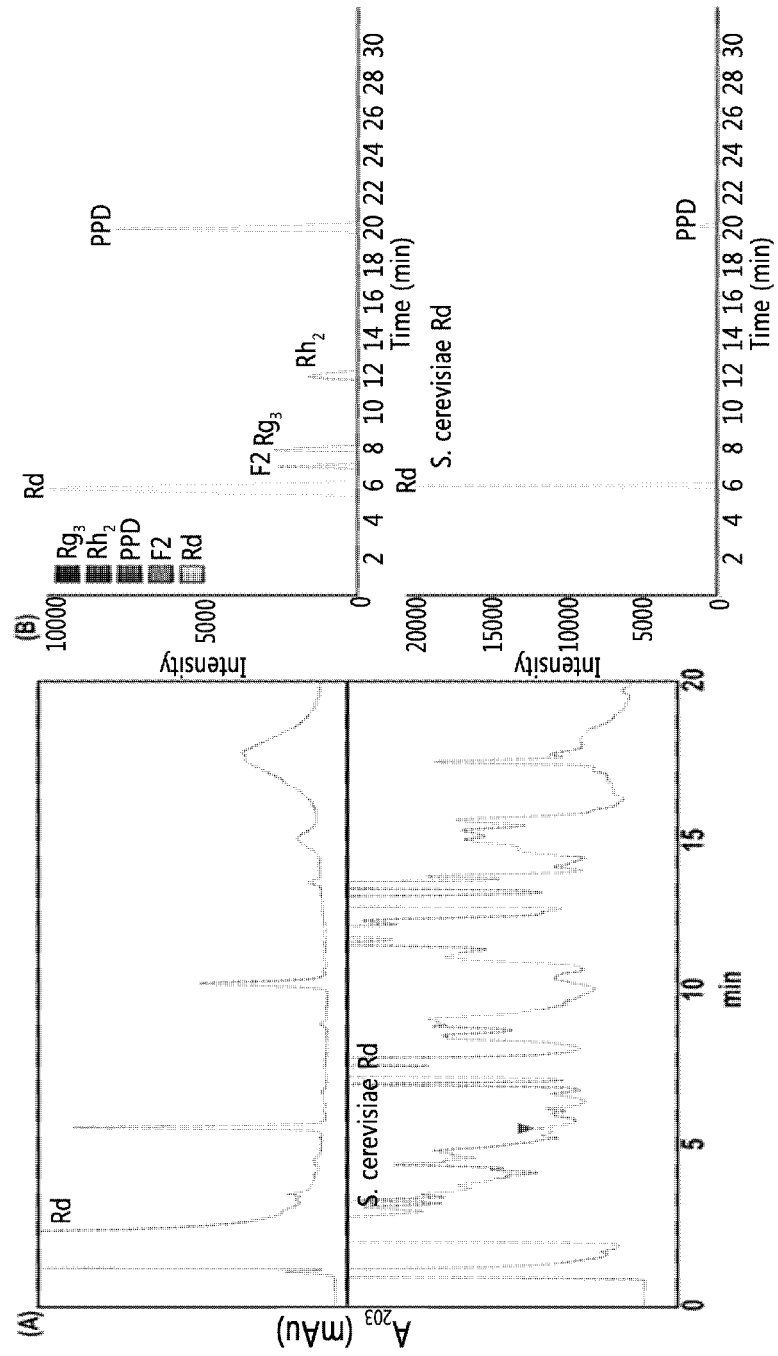

METHOD FOR GLYCOSYLATION OF GINSENOSIDE USING A GLYCOSYLTRANSFERASE DERIVED FROM PANAX GINSENG

CROSS REFERENCE TO RELATED APPLICATIONS

This application is a U.S. National Stage Application filed under 35 U.S.C. § 371 and claims priority to International Application No. PCT/KR/2015/004399, filed Apr. 30, 2015, which application claims priority to Korean Application No. 10-2014-0052728, filed Apr. 30, 2014, the disclosures of which are incorporated herein by reference in their entirety.

TECHNICAL FIELD

The present invention relates to a uridine diphosphate (UDP) glycosyltransferase protein which has glycosylation activity for a hydroxyl group located at the C-20 position of a protopanaxadiol (PPD)- or protopanaxatriol (PPT)-type ginsenoside, and a method for UDP glycosylation using the same.

BACKGROUND ART

Ginseng is one of the most popular medicinal plants widely used for improving health. The root of ginseng has been consumed as a herbal tea in the traditional medicine and is currently used in a variety of products including candies, instant teas, and tonic drinks. Ginsenosides, which are glycosylated triterpene compounds contained in ginseng, may provide many positive effects on health. In particular, the ginsenosides have been known to have various pharmacological effects such as enhancement of the immune system and revitalization of the body function, and more than 40 different ginsenosides have been identified from the root of ginseng. However, the difficulty in large-scale production of the individual ginsenosides remains as a major obstacle to investigation of the efficacy of each ginsenoside, e.g., its therapeutic effect on specific diseases, and commercial use of the identified ginsenosides.

Ginsenosides are glycosylated dammarene-type tetracyclic triterpenes and can be classified into three different groups based on their aglycone structures: protopanaxadiol (PPD)-type ginsenosides, protopanaxatriol (PPT)-type ginsenosides and oleanolic acid-type ginsenosides. These three groups can be further classified based on the position and number of sugar moieties (aglycones) attached to the C-3, C-6 and C-20 positions of the rings in the chemical structure by a glycosidic bond. PPDs and PPTs have different hydroxylation patterns. While the PPDs have —OH groups at the C-3, C-12 and C-20 positions, the PPTs have —OH groups at the C-3, C-6, C-12 and C-20 positions. The PPDs and PPTs can be glycosylated with glucose or other sugars to be converted into various ginsenosides. The glycosylated PPD-type ginsenosides include ginsenosides $Rb_1$, Rd, F2, $Rg_3$, $Rh_2$, compound K (C—K), $Rb_2$, Rc, compound MC (C-MC), compound Y (C—Y), etc., and the glycosylated PPT-type ginsenosides include ginsenosides $Rg_1$, $Rh_1$, F1, Rf, Re, $Rg_2$, etc.

The biosynthetic pathway of ginsenosides has been only partially identified. The ginsenosides are known to partially share the biosynthetic pathway with other triterpenes until oxidosqualene is synthesized by a series of condensation reactions of isopentenyl diphosphate and dimethylallyl diphosphate (DMADP) by the actions of IPP isomerase (IPI), GPP synthase (GPS), FPP synthase (FPS), squalene synthase (SS), and squalene epoxidase (SE) (Ajikumar et al. Science, 330, 70-74. 2010; Ro et al. Nature, 440, 940-943. 2006; Sun et al. BMC Genomics, 11, 262, 2010). Oxidosqualene is cyclized into dammarenediol-II by dammarenediol-II synthase (DS) which is a triterpene cyclase. Dammarenediol-II has hydroxyl groups at the C-3 and C-20 positions, and is converted to PPD by hydroxylation of the C-12 position by the p450 enzyme protopanaxadiol synthase (PPDS). PPDS can also be converted to PPT by hydroxylation at the C-6 position by another p450 protein, protopanaxatirol synthase (PPTS). PPD can be converted to various PPD-type ginsenosides by glycosylation at the C-3 and/or C-20 position(s), and PPT can be converted to various PPT-type ginsenosides by glycosylation at the C-6 and/or C-20 position(s).

Uridine diphosphate (UDP) glycosyltransferase (UGT) is an enzyme that catalyzes the transfer of a sugar moiety from a UDP-sugar to a wide variety of metabolites such as hormones and secondary metabolites. In general, UGT acts in the final step of the biosynthetic pathway in order to increase the solubility, stability, storage, biological activity or biological availability of metabolites. As recognized by the remarkable diversity of plant metabolites, each plant genome possesses hundreds of different UGTs. For example, a thale cress (*Arabidopsis thaliana*) plant model contains 107 UGTs that belong to 14 different groups (groups A to N) based on the amino acid sequences. However, although DS, PPDS, and PPTS have been reported as the enzymes involved in ginsenoside biosynthesis, little is known about whether UGT is involved in ginsenoside biosynthesis. Therefore, for production of specific ginsenosides, it is necessary to identify the UGTs, which use ginsenosides as substrates.

Different UGTs exhibit substrate specificity towards both sugar donors and sugar acceptors. For example, UGT78D2 transfers glucose from UDP-glucose to the C-3 position of a flavonol (kaempferol or quercetin) and an anthocyanin (cyanidin) in order to produce flavonol-3-O-glucosides and cyanidin-3-O-glucoside, respectively. It seems that such glycosylation is essential for in-vivo stability and storage of the compounds. On the other hand, UGT89C1 transfers rhanmnose from UDP-rhanmnose to the C-7 position of flavonol-3-O-glucoside in order to produce flavonol-3-O-glucoside-7-O-rhamnoside. Since UGT89C1 does not utilize UDP-glucose and anthocyanin-3-O-glucoside as substrates, it is known to exhibit different specificity towards the UDP-sugar and other acceptors from that of UGT78D2. As described, because different UGTs may have different substrate specificity and regioselectivity, it is necessary to investigate the substrate specificity and regioselectivity of the individual UGTs.

DISCLOSURE OF INVENTION

Technical Problem

The inventors of the present invention have made a lot of efforts to develop a novel UDP glycosyltransferase having substrate specificity and regioselectivity that can be used for biosynthesis of a particular ginsenoside. As a result, they have identified a novel glycosyltransferase, PgUGT71A1, from Korean ginseng and found out that the PgUGT71A1 can convert the PPD-type ginsenosides PPD, $Rh_2$ and $Rg_3$ to the ginsenosides C—K, F2, and Rd, respectively, and can convert PPT to F1. Since the protein has a glycosylation activity for a hydroxyl group at the C-20 position of PPD-and PPT-type ginsenosides, the inventors of the present invention have confirmed that it can be used to produce particular glycosylated ginsenosides and have completed the present invention.

Solution to Problem

An objective of the present invention is to provide a method for preparing a protopanaxadiol (PPD)- or protopanaxatriol (PPT)-type ginsenoside whose hydroxyl group at the C-20 position is glycosylated, comprising treating a UDP glycosyltransferase protein, a transformed cell which is introduced with a vector containing a polynucleotide encoding the protein or a fragment thereof and exhibits activity of the protein, an organism which contains the transformed cell, or a culture of the transformed cell to a PPD- or PPD-type ginsenoside having a hydroxyl group at the C-20 position.

Another objective of the present invention is to provide a composition for preparing a protopanaxadiol (PPD)- or protopanaxatriol (PPT)-type ginsenoside whose hydroxyl group at the C-20 position is glycosylated, which comprises one or more selected from the goup consisting of a uridine diphosphate (UDP) glycosyltransferase protein having glycosylation activity for a hydroxyl group at the C-20 position of a PPD- or PPT-type ginsenoside having the hydroxyl group at the C-20 position, a transformed cell which is introduced with a vector containing a polynucleotide encoding the protein or a fragment thereof, an organism which contains the transformed cell, or a culture of the transformed cell as an active ingredient.

Still another objective of the present invention is to provide a UDP glycosyl-transferase protein defined by the amino acid sequence of SEQ ID NO: 1, which has a selective glycosylation activity for a hydroxyl group at the C-20 position of a PPD- or PPT-type ginsenoside.

Still another objective of the present invention is to provide a polynucleotide which encodes the protein, an expression vector which contains the polynucleotide, a transformed cell which contains the expression vector or a fragment thereof, and an organism which contains the transformed cell.

Still another objective of the present invention is to provide an expression vector which contains polynucleotides encoding UDP glycosyltransferase proteins of DS, tHMGR, PPDS, and AtCPR proteins, respectively; a transformed cell for producing C—K which contains the expression vector or a fragment thereof; and an organism which contains the transformed cell.

Still another objective of the present invention is to provide an expression vector which contains polynucleotides encoding UDP glycosyltransferase proteins of DS, tHMGR, PPDS, AtCPR, and PPTS proteins, respectively; a transformed cell for producing F1 which contains the expression vector or a fragment thereof; and an organism which contains the transformed cell.

Still another objective of the present invention is to provide an expression vector which contains polynucleotides encoding UDP glycosyltransferase proteins of DS, tHMGR, PPDS, AtCPR, and PgUGT74A1 proteins, respectively; a transformed cell for producing F2 which contains the expression vector or a fragment thereof; and an organism which contains the transformed cell.

Still another objective of the present invention is to provide an expression vector which contains polynucleotides encoding UDP glycosyltransferase proteins of DS, tHMGR, PPDS, AtCPR, PgUGT74A1 and PgUGT94B 1 proteins, respectively; a transformed cell for producing Rd which contains the expression vector or a fragment thereof; and an organism which contains the transformed cell.

Advantageous Effects of Invention

Since the UDP glycosyltransferase of the present invention is a protein having an activity of selectively transferring a sugar to a hydroxyl group at the C-20 position of a PPD- or PPT-type ginsenoside, it may be usefully used for large-scale production of a ginsenoside having a sugar at the C-20 position, such as C—K, F2, Rd, and F1.

Additionally, in the present invention, the expression vector, and the transformed cell including the expression vector may be usefully used for large-scale production of particular ginsenosides by de novo synthesis of ginsenoside C—K (amount of novel synthesis; 4.5 mg/L), F1, F2, or Rd having a sugar at C-20 position.

BRIEF DESCRIPTION OF DRAWINGS

FIG. 1 shows the chemical structures of PPD- and PPT-type ginsenosides.

FIG. 2 shows that PgUGT71A1, a UDP glycosyltransferase, has a glycosylation activity of attaching UDP-glucose to a hydroxyl group at the C-20 position of PPD-type and PPT-type ginsenosides. Specifically, a result of analyzing the conversion of PPD to compound K (C—K), $Rg_3$ to Rd, $Rh_2$ to F2, and PPT to F1 by PgUGT71A1 through thin-layer chromatography (TLC; top) and high performance liquid chromatography (HPLC; bottom) is shown.

FIG. 3 shows the results of demonstrating the increased expression of the PgUGT71A1 of the present invention in the leaves and roots of ginseng treated with methyl jasmonate (MeJA) via real-time PCR.

FIG. 4 shows the results of demonstrating the increased expression of the PgUGT71A1 of the present invention in the leaf and root of ginseng treated with methyl jasmonate (MeJA) through NGS.

FIG. 5 shows a prepared platform plasmid called pRS306-MET3p-ERG7-CYClter(A), and the results of PCR amplification of a cassette from URA3 region to CYC1 terminator using ERG7 knock down-F and ERG7 knock-down-B primers(B).

FIG. 6 shows a biosynthetic pathway of C—K in *S. cerevisiae* MET3p-ERG7 by introduction of pRS424-DS, pRS426-tHMG1, pRS425-PPD containing PPDS and AtCPR, and pRS423-C—K containing PgUGT71A1.

FIG. 7 shows the results of HPLC and LC-MS/MS analyses of demonstrating that the formation of a new peak at 11.97 min, which is identical to the retention time of C—K in HPLC, by the substances produced in a yeast containing PgUGT71A1(A), and the retention time of C—K produced by a yeast, analyzed by LC-MS/MS analysis(B).

FIG. 8 shows a biosynthetic pathway of ginsenoside F1 in *S. cerevisiae* MET3p-ERG7 by introduction of pRS424-DS, pRS426-tHMG1, pRS425-PPD containing PPDS and AtCPR, pRS423-F1 containing PgUGT71A1 and PgPPTS.

FIG. 9 shows the results of HPLC and LC-MS/MS analyses of demonstrating that the formation of a new peak at 6.01 min, which is identical to the retention time of F1 in HPLC, by the substances produced in a yeast containing PgUGT71A1 and PgPPTS(A), and the retention time of F1 produced by a yeast, analyzed by LC-MS/MS analysis(B).

FIG. 10 shows a biosynthetic pathway of ginsenoside F2 in *S. cerevisiae* MET3p-ERG7 by introduction of pRS424-

DS, pRS426-tHMG1, pRS425-PPD containing PPDS and AtCPR, pRS423-F2 containing PgUGT74A1 and PgUGT71A1.

FIG. 11 shows the results of HPLC and LC-MS/MS analyses of demonstrating that the formation of a new peak at 7.81 min, which is identical to the retention time of F2 in HPLC, by the substances produced in a yeast containing PgUGT74A1 and PgUGT71A1(A), and the retention time of F2 produced by a yeast, analyzed by LC-MS/MS analysis (B).

FIG. 12 shows a biosynthetic pathway of ginsenoside Rd in S. cerevisiae MET3p-ERG7 by introduction of pRS424-DS, pRS426-tHMG1, pRS425-PPD containing PPDS and AtCPR, pRS423-Rd containing PgUGT74A1, PgUGT94B1 and PgUGT71A1.

FIG. 13 shows the results of HPLC and LC-MS/MS analyses of demonstrating that the formation of a new peak at 5.88 min, which is identical to the retention time of Rd in HPLC, by the substances produced in a yeast containing PgUGT74A1, PgUGT94B1, and PgUGT71A1(A), and the retention time of Rd produced by a yeast, analyzed by LC-MS/MS analysis(B).

BEST MODE FOR CARRYING OUT THE INVENTION

In an aspect, the present invention provides a method for preparing a protopanaxadiol (PPD)- or protopanaxatriol (PPT)-type ginsenoside whose hydroxyl group at the C-20 position is glycosylated, comprising treating a UDP glycosyltransferase protein, a transformed cell which is introduced with a vector containing a polynucleotide encoding the protein or a fragment thereof and exhibits activity of the protein, an organism which contains the transformed cell, or a culture of the transformed cell to a PPD- or PPD-type ginsenoside having a hydroxyl group at the C-20 position.

In the present invention, the term, "uridine diphosphate (UDP) glycosyltransferase" refers to an enzyme that has an activity of transferring a monosaccharide moiety from a glycosyl donor to a glycosyl acceptor, in particular, an enzyme that utilizes a UDP-sugar as a glycosyl donor. In the present invention, the term UDP glycosyltransferase may be used interchangeably with 'UGT'. Since little is known about the ginsenoside UDP glycosyltransferases and since different enzymes having UDP glycosyltransferase activity have different substrate specificity and regioselectivity, it needs to be determined whether the enzyme is a UDP glycosyltransferase which specifically acts on a particular ginsenoside which is a ginseng saponin.

The inventors of the present invention have identified a novel UDP glycosyl-transferase derived from ginseng (Panax ginseng C. A. Meyer), which is capable of selectively transferring a sugar moiety to a hydroxyl (—OH) group at the C-20 position of a PPD-type ginsenoside or a PPT-type ginsenoside, for the first time. The UDP glycosyltransferase identified by the inventors of the present invention has an activity of selectively transferring the sugar moiety of UDP-glucose to a hydroxyl group at the C-20 position of a PPD-type ginsenoside or a PPT-type ginsenoside. Accordingly, the UDP glycosyltransferase identified in the present invention can convert the PPD-type ginsenosides PPD, $Rh_2$ and $Rg_3$ to the ginsenosides C—K, F2 and Rd, respectively, and can also convert PPT to F1 by transferring a sugar moiety to the hydroxyl group at the C-20 position. A ginsenoside UDP glycosyltransferase having such activity has never been known and has been first identified by the inventors of the present invention.

The UDP glycosyltransferase identified in the present invention is a UDP glycosyltransferase derived from Korean ginseng (Panax ginseng C. A. Meyer) and may be defined by the amino acid sequence of SEQ ID NO: 1. In an exemplary embodiment of the present invention, the UDP glycosyltransferase defined by the amino acid sequence of SEQ ID NO: 1 is designated as 'PgUGT71A1'.

The UDP glycosyltransferase of the present invention may refer to not only a protein having the amino acid sequence of SEQ ID NO: 1 but also a protein having an amino acid sequence having similarity of 70% or higher, preferably 80% or higher, more preferably 90% or higher, even more preferably 95% or higher, even much more v98% or higher, and most preferably 99% or higher, to the amino acid sequence of SEQ ID NO: 1 and being capable of substantially transferring a sugar to a hydroxyl group at the C-20 position of a PPD- or PPT-type ginsenoside, without limitation. In addition, if the protein having the sequence similarity has substantially the same or comparable biological activity as UDP glycosyltransferase, a variant of the protein which has a portion of the sequence deleted, modified, substituted or added is included in the scope of the present invention.

The term "similarity" is intended to indicate the degree of similarity to the amino acid sequence of a wild-type protein or a nucleotide sequence that encodes the same, and includes sequences having similarity of the above-described percentage or higher to the amino acid sequence or nucleotide sequence of the present invention. Comparison of the similarity may be conducted with the naked eye or using a commercially readily available comparison program.

Since the UDP glycosyltransferase of the present invention has an activity of selectively transferring a sugar to the C-20 position of a PPD- or PPT-type ginsenoside, specifically to the C-20 position having a hydroxyl group, it may be used to prepare a glycosylated ginsenoside from a PPD- or PPT-type ginsenoside having a hydroxyl group at the C-20 position.

In the present invention, the term "PPD-type ginsenoside" refers to a dammarane-type saponin, which is a PPD having —OH groups at the C-3, C-12 and C-20 positions or a ginsenoside having the —OH groups of the PPD glycosylated. Examples of the PPD-type ginsenoside that can be glycosylated by the glycosyltransferase of the present invention include PPD, $Rg_3$, $Rh_2$, etc. having a hydroxyl group at the C-20 position. However, any PPD-type ginsenoside that can be glycosylated by the UDP glycosyltransferase of the present invention may be included without limitation.

In the present invention, the term "PPT-type ginsenoside" refers to a dammarane-type saponin, which is a PPT having —OH groups at the C-3, C-6, C-12 and C-20 positions or a ginsenoside having the —OH groups of the PPT glycosylated. Examples of the PPT-type ginsenoside that can be glycosylated by the glycosyltransferase of the present invention include a PPT having a hydroxyl group at the C-20 position and not having a sugar at the C-6 position. However, any PPT-type ginsenoside that can be glycosylated by the UDP glycosyltransferase of the present invention is included without limitation.

The PPD-type or PPT-type ginsenoside may be an isolated and purified ginsenoside, or a ginsenoside included in a powder or extract of ginseng or red ginseng. That is, a powder or extract of ginseng or red ginseng containing a saponin may be used directly as a ginsenoside to carry out the method of the present invention. Alternatively, a chemically synthesized ginsenoside may be used. Various types of known ginseng may be used in the present invention.

Examples include Korean ginseng (*Panax ginseng*), American ginseng (*P. quinquefolius*), notoginseng (*P. notoginseng*), Japanese ginseng (*P. japonicus*), dwarf ginseng (*P. trifolium*), Himalayan ginseng (*P. pseudoginseng*) and Vietnamese ginseng (*P. vietnamensis*), although not being limited thereto. The chemical structure of the PPD-type or PPT-type ginsenoside is shown in FIG. 1.

In the present invention, the term "glycosylated ginsenoside" refers to a ginsenoside having a monosaccharide or a higher saccharide attached to the hydroxyl group of a non-sugar component (aglycone) that constitutes the ginsenoside. For the purpose of the present invention, the glycosylated ginsenoside includes any glycosylated ginsenoside without limitation as long as it is a ginsenoside glycosylated as a sugar, preferably glucose, is transferred to the C-20 position of the PPD- or PPT-type ginsenoside by the UDP glycosyltransferase of the present invention. Examples include compound K (C—K), F2, Rd or PPT glycosylated by the glycosyltransferase of the present invention from PPD, $Rh_2$, $Rg_3$ or F1, respectively, although not being limited thereto.

For preparing a glycosylated ginsenoside by converting a PPD- or PPT-type ginsenoside having a hydroxyl group at the C-20 position, a transformed cell which contains an expression vector containing a polynucleotide encoding the UDP glycosyltransferase or a fragment thereof and exhibits activity of the UDP glycosyltransferase, an organism which contains the transformed cell, or a culture of the transformed cell may be used.

The polynucleotide encoding the UDP glycosyltransferase protein may be preferably a polynucleotide defined by a nucleotide sequence of SEQ ID NO: 2. In addition to the polynucleotide having a nucleotide sequence of SEQ ID NO: 2, any polynucleotide with a nucleotide sequence having a sequence similarity of 70% or higher, preferably 80% or higher, more preferably 90% or higher, even more preferably 95% or higher, most preferably 98% or higher, to the nucleotide sequence of SEQ ID NO: 2 and being capable of substantially encoding a protein having activity of the PgUGT71A1 protein is included, without limitation.

The expression vector containing the polynucleotide of the present invention refers to a nucleic acid construct containing essential regulatory elements which are operably linked to express an inserted nucleic acid, as an expression vector capable of expressing the target protein in a suitable host cell. The desired target protein can be obtained by transforming or transfecting the prepared recombinant vector into the host cell.

The expression vector containing the polynucleotide provided by the present invention includes *E. coli*-derived plasmids (pYG601BR322, pBR325, pUC118, and pUC119), Bacillus subtilis-derived plasmids (pUB110 and pTP5), yeast-derived plasmids (YEp13, YEp24, and YCp50) and Ti plasmids that may be used in Agrobacterium-mediated transformation, although not particularly limited thereto. Specific examples of phage DNAs include λ-phages (Charon4A, Charon21A, EMBL3, EMBL4, λgt10, λgt11 and λZAP). In addition, an animal virus such as retrovirus, adenovirus or vaccinia virus, an insect virus such as baculovirus, a double-stranded plant virus (e.g., CaMV), a single-stranded virus, or a viral vector derived from geminivirus may be used.

Moreover, as the vector of the present invention, a transcriptional activator protein (e.g., B42)-linked fusion plasmid (e.g., pJG4-5) may be used. In addition, for easier purification of the target protein obtained in the present invention, the plasmid vector may further include other sequences, if necessary. For example, the fusion plasmid may contain a tag such as GST, GFP, His-tag, Myc-tag, etc., although not limited thereto. In an exemplary embodiment of the present invention, a pGEX4T-1 vector which is a GST gene-fused vector may be used to construct the expression vector which contains the polynucleotide encoding the UDP glycosyltransferase protein.

In addition, a fusion protein expressed by a vector containing a fusion sequence may be purified by affinity chromatography. For example, when a glutathione S-transferase is fused, glutathione which is a substrate of the enzyme may be used. And, when hexahistidine is fused, the target protein may be easily recovered by using a Ni—NTA Hisbind resin column (Novagen, USA).

In order to insert the polynucleotide of the present invention into the vector, a purified DNA may be cleaved using appropriate restriction enzymes and then inserted into the restriction sites or cloning sites of a suitable vector DNA.

The polynucleotide encoding the UDP glycosyltransferase of the present invention protein may be operably linked to the vector. The vector of the present invention may further contain, in addition to a promoter and the nucleic acid of the present invention, a cis element such as an enhancer, a splicing signal, a poly-A addition signal, a selection marker, a ribosome-binding sequence (SD sequence), etc. As examples of the selection marker, a chloramphenicol resistance gene, a chloramphenicol resistance gene, dihydrofolate reductase, a neomycin resistance gene, etc. may be used. However, the additional elements to be operably linked are not limited to these examples. In the present invention, the term "transformation" refers to introduction of a DNA into a host cell such that the DNA can be replicated as an extra-chromosomal element or by chromosomal integration. That is, transformation refers to a phenomenon of artificial alteration of genes by introducing a foreign DNA into the cell.

The expression vector which contains the polynucleotide encoding the UDP glycosyltransferase of the present invention protein or a fragment of the expression vector may be introduced into a host cell through transformation. As used herein, a fragment of the expression vector refers to a fragment of the expression vector which contains the portion of the polynucleotide that encodes the UDP glycosyltransferase protein such that the activity of the UDP glycosyltransferase protein can be conferred to the host cell. For example, it may be the T-DNA of a Ti plasmid transferred into a host cell in *Agrobacterium*-mediated transformation, although not limited thereto.

The transformation of the present invention may be performed by any transformation method and can be easily performed according to the method commonly employed in the art. In general, examples of the transformation method include $CaCl_2$ precipitation, a Hanahan method which is an improved $CaCl_2$ method using dimethylsulfoxide (DMSO) as a reducing material, electroporation, calcium phosphate precipitation, protoplast fusion, agitation using silicon carbide fiber, *Agrobacterium*-mediated transformation, PEG-mediated transformation, dextran sulfate-, lipofectamine- and desiccation/inhibition-mediated transformation, and so forth. However, the method for transforming the vector containing the polynucleotide which encodes the UDP glycosyltransferase of the present invention is not limited to the above examples, and the transformation or transfection methods typically employed in the art may be used without limitation.

In the present invention, the host cell is not particularly limited as long as it is able to express the polynucleotide of the present invention. Specific examples of the host that can be used in the present invention include bacteria belonging to the genus *Escherichia* such as *E. coli,* bacteria belonging to the *Bacillus* genus such as *Bacillus subtilis*, bacteria belonging to the *Pseudomonas* genus such as *Pseudomonas putida*, yeasts such as *Saccharomyces cerevisiae* or *Schizosaccharomyces pombe*, animal cells, plant cells and insect cells. Specific examples of the *E. coli* strain that can be used in the present invention include CL41 (DE3), BL21 or HB101, and specific examples of the *Bacillus subtilis* that can be used in the present invention include WB700 or LKS87.

The organism that can contain the transformed cell which is introduced with the expression vector encoding the polynucleotide of the present invention or a fragment thereof may be, for example, tobacco, thale cress, potato, ginseng, sesame, citron, daisy, etc., although not particularly limited thereto.

Any promoter can be used as the promoter of the present invention as long as it enables expression of the nucleic acid of the present invention in the host cell. For example, an *E. coli*- or phage-derived promoter such as a trp promoter, a lac promoter, a PL promoter or a PR promoter, an *E. coli*-infecting phage-derived promoter such as a T7 promoter, a CaMV35S promoter, a MAS promoter or a histone promoter may be used. Also, an artificially modified promoter such as a tac promoter may be used.

The transformant wherein the expression vector which contains the polynucleotide encoding the UDP glycosyltransferase of the present invention protein is introduced by transformation has a selective glycosylation activity for a hydroxyl group at the C-20 position of a PPD- or PPT-type ginsenoside, specifically a glycosylation activity of converting PPD to C—K, converting $Rh_2$ to F2, converting $Rg_3$ to Rd or converting PPT to F1, although not limited thereto.

In the present invention, the term "culture of the transformed cell" refers to a product obtained by culturing the transformed cell according to a known method of culturing microorganisms. The term culture is used in a broad concept, including a culture containing the transformed cell and one obtained by removing the transformed cell from the culture containing the transformed cell through, e.g., centrifugation.

Since the culture contains the UDP glycosyltransferase of the present invention protein, it has an activity of converting a PPD- or PPT-type ginsenoside to a glycosylated ginsenoside. For example, it may convert PPD to C—K, convert $Rh_2$ to F2, convert $Rg_3$ to Rd, and convert PPT to F1.

Since the UDP glycosyltransferase of the present invention protein, a transformed cell which is introduced with an expression vector containing a polynucleotide encoding the protein or a fragment of the expression vector and exhibits activity of the protein, an organism containing the transformed cell, or a culture of the transformed cell may be used to convert a PPD- or PPT-type ginsenoside having a hydroxyl group at the C-20 position to a glycosylated ginsenoside, the method according to the present invention may be usefully used in the fields where ginsenosides with the C-20 position glycosylated are required, particularly where the ginsenosides such as ginsenosides C—K, F2, Rd, F1, etc., are required.

The inventors of the present invention have identified a novel UDP glycosyltransferase which has an activity of selectively transferring a glucose moiety of UDP-glucose to a hydroxyl group at the C-20 position of a PPD- or PPT-type ginsenoside and has an amino acid sequence of SEQ ID NO: 1 from Korean ginseng (*Panax ginseng* C. A. Meyer) and have named it as PgUGT71A1 (Example 1). In order to investigate the enzymatic activity of the PgUGT71A1 protein, PPD, $Rg_3$, $Rh_2$ and PPT, which are representative PPD- or PPT-type ginsenosides having hydroxyl groups at the C-20 position, were reacted with the PgUGT71A1 of the present disclosure and their conversion activity was determined. As a result, the PgUGT71A1 of the present invention converted PPD to C—K, $Rg_3$ to Rd, $Rh_2$ to F2, and PPT to F1, suggesting that it has an activity of converting a glucose moiety to a hydroxyl group at the C-20 position of PPD-and PPT-type ginsenosides (FIG. 2). In addition, it was found out that the expression of the protein is enhanced by methyl jasmonate (MeJA), which is known to be expressed in both the leaf and root of ginseng and to enhance the expression of the biosynthetic genes of ginseng (FIGS. 3 and 4). These results suggest that the PgUGT71A1 of the present invention is involved in the biosynthesis of ginsenosides, particularly in the biosynthesis of C—K, Rd, F2, F1, etc., and the protein may be used in a process of bioconverting C—K, Rd, F2, F1, etc., through glycosylation at the C-20 position.

In another aspect, the present invention provides a composition for preparing a protopanaxadiol (PPD)- or protopanaxatriol (PPT)-type ginsenoside whose hydroxyl group at the C-20 position is glycosylated, which comprises one or more selected from the goup consisting of a uridine diphosphate (UDP) glycosyltransferase protein having glycosylation activity for a hydroxyl group at the C-20 position of a PPD- or PPT-type ginsenoside having the hydroxyl group at the C-20 position, a transformed cell which is introduced with a vector containing a polynucleotide encoding the protein or a fragment thereof, an organism which contains the transformed cell, or a culture of the transformed cell as an active ingredient.

The UDP glycosyltransferase protein, the transformed cell, the organism, the PPD-type or PPT-type ginsenoside and the glycosylated ginsenoside are the same as described above.

In another aspect, the present invention provides a UDP glycosyltransferase protein defined by the amino acid sequence of SEQ ID NO: 1, which has glycosylation activity for a hydroxyl group at the C-20 position of a PPD- or PPT-type ginsenoside.

The UDP glycosyltransferase protein and the amino acid sequence of SEQ ID NO: 1 are the same as described above.

The protein may be one that converts PD to C—K, $Rh_2$ to F2, $Rg_3$ to Rd, and PPT to F1.

In another aspect, the present invention provides an expression vector, which further includes polynucleotides encoding dammarenediol-II synthase (DS), truncated HMG-CoA reductase (tHMGR), protopanaxadiol synthase (PPDS), and *Arabidopsis thaliana* cytochrome p450 reductase (AtCPR) proteins, respectively, in addition to the expression vector including the polynucleotide encoding the UDP glycosyltransferase protein; and a transformed cell for producing C—K including the expression vector or a fragment thereof.

The UDP glycosyltransferase protein, the expression vector, and the transformed cell are the same as described above.

The dammarenediol-II synthase (DS), being a tritrpenecyclase, refers to an enzyme which cyclizes oxidosqualene into dammarenediol-II. The DS may be defined by an amino acid sequence described my SEQ ID NO: 29. Any protein variants having a deletion, a modification, a substitution, or an addition in part of their amino acid sequences therein may be included without limitation within the scope of the present invention, as long as the DS variant has an amino acid sequence having similarity of 70% or higher, preferably 80% or higher, more preferably 90% or higher, even more preferably 95% or higher, even much more preferably 98% or higher, and most preferably 99% or higher, to the amino acid sequence of SEQ ID NO: 29, and has a biological activity substantially the same as or corresponding to that of the DS.

The polynucleotide encoding the DS protein may be preferably a polynucleotide defined by the nucleotide sequence described in SEQ ID NO: 30 or SEQ ID NO: 31 optimized for codon usage of E. coli. Any polynucleotide variants having a deletion, a modification, a substitution, or an addition in part of their nucleotide sequences therein may be included without limitation within the scope of the present invention, as long as the variant has an nucleotide sequence having similarity of 70% or higher, preferably 80% or higher, more preferably 90% or higher, even more preferably 95% or higher, and even much more preferably 98% or higher, to the nucleotide sequence of SEQ ID NO: 30 or SEQ ID NO: 31, which encodes a protein having a biological activity substantially the same as that of the DS protein.

The truncated HMG-CoA reductase (tHMGR) is an important enzyme controlling in vivo synthesis of Z10 or cholesterol, and refers to an enzyme that converts HMG-CoA to mevalonate during the process of cholesterol synthesis. The tHMGR may be defined by an amino acid sequence described in SEQ ID NO: 32. Any protein variants having a deletion, a modification, a substitution, or an addition in part of their amino acid sequences therein may be included without limitation within the scope of the present invention, as long as the tHMGR variant has an amino acid sequence having similarity of 70% or higher, preferably 80% or higher, more preferably 90% or higher, even more preferably 95% or higher, even much more preferably 98% or higher, and most preferably 99% or higher, to the amino acid sequence of SEQ ID NO: 32, which has a biological activity substantially the same as or corresponding to that of the tHMGR.

The polynucleotide encoding the tHMGR protein may be preferably a polynucleotide defined by the amino acid sequence described in SEQ ID NO: 33. Any polynucleotide variants having a deletion, a modification, a substitution, or an addition in part of their nucleotide sequences therein may be included without limitation within the scope of the present invention, as long as the variant has an nucleotide sequence having similarity of 70% or higher, preferably 80% or higher, more preferably 90% or higher, even more preferably 95% or higher, and even much more preferably 98% or higher, to the nucleotide sequence of SEQ ID NO: 33, which encodes a protein having a biological activity substantially the same as that of the tHMGR protein.

The protopanaxadiol synthase (PPDS) is a p450 enzyme which converts the C-12 position of dammarenediol-II to PPD by hydroxylation. The PPDS may be defined by an amino acid sequence described in SEQ ID NO: 34. Any protein variants having a deletion, a modification, a substitution, or an addition in part of their amino acid sequences therein may be included without limitation within the scope of the present invention, as long as the PPDS variant has an amino acid sequence having similarity of 70% or higher, preferably 80% or higher, more preferably 90% or higher, even more preferably 95% or higher, even much more preferably 98% or higher, and most preferably 99% or higher, to the amino acid sequence of SEQ ID NO: 34, which has a biological activity substantially the same as or corresponding to that of the PPDS.

The polynucleotide encoding the PPDS protein may be preferably a polynucleotide defined by the nucleotide sequence described in SEQ ID NO: 35. Any polynucleotide variants having a deletion, a modification, a substitution, or an addition in part of their nucleotide sequences therein may be included without limitation within the scope of the present invention, as long as the variant has an nucleotide sequence having similarity of 70% or higher, preferably 80% or higher, more preferably 90% or higher, even more preferably 95% or higher, and even much more preferably 98% or higher, to the nucleotide sequence of SEQ ID NO: 35, which encodes a protein having a biological activity substantially the same as that of the PPDS protein.

The Arabidopsis thaliana cytochrome p450 reductase (AtCPR) may be used as having the same meaning as cytochrome p450 reductase. The AtCPR may be defined by an amino acid sequence described in SEQ ID NO: 36. Any protein variants having a deletion, a modification, a substitution, or an addition in part of their amino acid sequences therein may be included without limitation within the scope of the present invention, as long as the AtCPR vatiant has an amino acid sequence having similarity of 70% or higher, preferably 80% or higher, more preferably 90% or higher, even more preferably 95% or higher, even much more preferably 98% or higher, and most preferably 99% or higher, to the amino acid sequence of SEQ ID NO: 36, which has a biological activity substantially the same as or corresponding to that of the AtCPR.

The polynucleotide encoding the AtCPR protein may be preferably a polynucleotide defined by the nucleotide sequence described in SEQ ID NO: 37 or SEQ ID NO: 38 optimized for codon usage of E. coli. Any polynucleotide variants having a deletion, a modification, a substitution, or an addition in part of their nucleotide sequences therein may be included without limitation within the scope of the present invention, as long as the variant has an nucleotide sequence having similarity of 70% or higher, preferably 80% or higher, more preferably 90% or higher, even more preferably 95% or higher, and even much more preferably 98% or higher, to the nucleotide sequence of SEQ ID NO: 37 or SEQ ID NO: 38, which encodes a protein having a biological activity substantially the same as that of the AtCPR protein.

In an exemplary embodiment of the present invention, S. cerevisiae C—K strain having a C—K biosynthesis pathway of C—K was constructed by simultaneously introducing pRS424 DS, pRS426 tHMG1, pRS425 PPD containing PPDS and AtCPR, and pRS423 C—K containing PgUGT71A1 into S. cerevisiae MET3p-ERG7 via lithium acetate method (FIG. 6), and the S. cerevisiae C—K strain was cultured via fed-batch fermentation for 10 d (OD600≈80) in the presence of methionine. Yeast cells were harvested by centrifugation and disrupted by sonication. Ginsenosides were extracted using MtOH and purified using Sep-PAK. Purified ginsenosides were analyzed by HPLC and LC-MS/MS. As a result, the yeast harboring PgUGT71A1 produced a new peak at 11.97 min, which is identical to the retention time of C—K in HPLC((A) of FIG. 7), whereas the observed retention time of products in LC-MS/MS detected by MRM was 11.46 min with the transition at 645.4→23.2 ((B) of FIG. 7). These results indicate that the PgUGT71A1 enable the de novo production of ginsenosides through yeast fermentation (4.5 mg/L).

Accordingly, the present invention can provide an expression vector, which further includes polynucleotides encoding UDP glycosyltransferase proteins of DS, tHMGR, PPDS, and AtCPR proteins, respectively, and a transformed cell for producing C—K including the expression vector or a fragment thereof.

The transformed cell may be a yeast, but is not limited thereto.

In another aspect, the present invention provides an expression vector, which further includes polynucleotides encoding dammarenediol-II synthase (DS), truncated HMG-CoA reductase (tHMGR), protopanaxadiol synthase (PPDS), *Arabidopsis thaliana* cytochrome p450 reductase (AtCPR), and protopanaxatriol synthase (PPTS) proteins, respectively, in addition to the expression vector including the polynucleotide encoding the UDP glycosyltransferase protein; and a transformed cell for producing F1 including the expression vector or a fragment thereof.

The dammarenediol-II synthase (DS), truncated HMG-CoA reductase (tHMGR), protopanaxadiol synthase (PPDS), and *Arabidopsis thaliana* cytochrome p450 reductase (AtCPR) are the same as described above.

The UDP glycosyltransferase protein, the expression vector, and the transformed cell are the same as described above.

The protopanaxatriol synthase (PPTS) is another p450 protein which converts the C-6 position of PPDS to PPT by hydroxylation. The PPTS may be defined by an amino acid sequence described in SEQ ID NO: 39. Any protein variants having a deletion, a modification, a substitution, or an addition in part of their amino acid sequences therein may be included without limitation within the scope of the present invention, as long as the PPTS variant has an amino acid sequence having similarity of 70% or higher, preferably 80% or higher, more preferably 90% or higher, even more preferably 95% or higher, even much more preferably 98% or higher, and most preferably 99% or higher, to the amino acid sequence of SEQ ID NO: 39, which has a biological activity substantially the same as or corresponding to that of the PPTS.

The polynucleotide encoding the PPTS protein may be preferably a polynucleotide defined by the nucleotide sequence described in SEQ ID NO: 40 or SEQ ID NO: 41 optimized for codon usage of yeast. Any polynucleotide variants having a deletion, a modification, a substitution, or an addition in part of their nucleotide sequences therein may be included without limitation within the scope of the present invention, as long as the variant has an nucleotide sequence having similarity of 70% or higher, preferably 80% or higher, more preferably 90% or higher, even more preferably 95% or higher, and even much more preferably 98% or higher, to the nucleotide sequence of SEQ ID NO: 40 or SEQ ID NO: 41, which encodes a protein having a biological activity substantially the same as that of the PPTS protein.

In an exemplary embodiment of the present invention, *S. cerevisiae* F1 strain having a biosynthesis pathway of ginsenoside F1 was constructed by simultaneously introducing pRS424 DS, pRS426 tHMG1, pRS425 PPD containing PPDS and AtCPR, pRS423 F1 containing PgUGT71A1 and PgPPTS into *S. cerevisiae* MET3p-ERG7 via lithium acetate method (FIG. 8), and the *S. cerevisiae* F1 strain was cultured via fed-batch fermentation for 10 d (OD600≈80) in the presence of methionine. Additionally, yeast cells were harvested by centrifugation and disrupted by sonication. Ginsenosides were extracted using BtOH and then evaporated BtOH. Finally, ginsenoside F1 was re-extracted by MtOH and the extracted ginsenoside was analyzed by HPLC and LC-MS/MS. As a result, the yeast harboring PgUGT71A1 and PgPPTS produced a new peak at 6.01 min, which is identical to the retention time of F1 in HPLC((A) of FIG. 9), whereas the observed retention time of products in LC-MS/MS detected by MRM was 6.13 min with the transition at 661.5→203 ((B) of FIG. 9). These results indicate that the PgUGT71A1 and PgPPTS enable the de novo production of ginsenoside F1 through yeast fermentation.

Accordingly, the present invention can provide an expression vector, which further includes polynucleotides encoding UDP glycosyltransferase proteins of DS, tHMGR, PPDS, AtCPR, and PPTS proteins, respectively, and a transformed cell for producing F1 including the expression vector or a fragment thereof.

The transformed cell may be a yeast, but is not limited thereto.

In another aspect, the present invention provides an expression vector, which further includes polynucleotides encoding dammarenediol-II synthase (DS), truncated HMG-CoA reductase (tHMGR), protopanaxadiol synthase (PPDS), *Arabidopsis thaliana* cytochrome p450 reductase (AtCPR), and panax ginseng UDP glycosyltransferase 74A1 (PgUGT74A1) proteins, respectively, in addition to the expression vector including the polynucleotide encoding the UDP glycosyltransferase protein; and a transformed cell for producing F2 including the expression vector or a fragment thereof.

The dammarenediol-II synthase (DS), truncated HMG-CoA reductase (tHMGR), protopanaxadiol synthase (PPDS), and *Arabidopsis thaliana* cytochrome p450 reductase (AtCPR) are the same as described above.

The UDP glycosyltransferase protein, the expression vector, and the transformed cell are the same as described above.

Panax ginseng UDP glycosyltransferase 74A1 (PgUGT74A1) is a UDP glycosyltransferase acting specifically on PPD and C—K, which are PPD-type ginsenosides, to cause O-glycosylation of the C-3 position thereby converting PPD and C—K into $Rh_2$ and F2, respectively. The PgUGT74A1 may be defined by the amino acid sequence described in KR Pat. No. 10-1479615. Any protein variants having a deletion, a modification, a substitution, or an addition in part of their amino acid sequences therein may be included without limitation within the scope of the present invention, as long as the PgUGT74A1 variant has an amino acid sequence having similarity of 70% or higher, preferably 80% or higher, more preferably 90% or higher, even more preferably 95% or higher, even much more preferably 98% or higher, and most preferably 99% or higher, to the amino acid sequence described in KR Pat. No. 10-1479615, which has a biological activity substantially the same as or corresponding to that of the PgUGT74A 1.

The polynucleotide encoding the PgUGT74A1 protein may be preferably a polynucleotide defined by the nucleotide sequence described in KR Pat. No. 10-1479615, and any polynucleotide variants having a deletion, a modification, a substitution, or an addition in part of their nucleotide sequences therein may be included without limitation within the scope of the present invention, as long as the variant has an nucleotide an nucleotide sequence having similarity of 70% or higher, preferably 80% or higher, more preferably 90% or higher, even more preferably 95% or higher, and even much more preferably 98% or higher, to the nucleotide sequence described in KR Pat. No. 10-1479615, which encodes a protein having a biological activity substantially the same as that of the PgUGT74A1 protein.

In an exemplary embodiment of the present invention, *S. cerevisiae* F2 strain having a biosynthesis pathway of ginsenoside F2 was constructed by simultaneously introducing pRS424 DS, pRS426 tHMG1, pRS425 PPD containing PPDS and AtCPR, pRS423 F2 containing PgUGT74A1 and PgUGT71A1 into *S. cerevisiae* MET3p-ERG7 via lithium acetate method (FIG. 10), and the *S. cerevisiae* F2 strain was cultured via fed-batch fermentation for 10 d (OD600≈80) in the presence of methionine. Additionally, yeast cells were harvested by centrifugation and disrupted by sonication. Ginsenosides were extracted using BtOH and then evaporated BtOH. Finally, ginsenoside F2 was re-extracted by MtOH and the extracted ginsenoside was analyzed by HPLC and LC-MS/MS. As a result, the yeast harboring PgUGT74A1 and PgUGT71A1 produced a new peak at 7.81 min, which is identical to the retention time of F2 in HPLC((A) of FIG. 11), whereas the observed retention time of products in LC-MS/MS detected by MRM was 7.35 min with the transition at 807.5→627.5 ((B) of FIG. 11). These results indicate that the PgUGT74A1 and PgUGT71A1 enable the de novo production of ginsenoside F2 through yeast fermentation.

Accordingly, the present invention can provide an expression vector, which further includes polynucleotides encoding UDP glycosyltransferase proteins of DS, tHMGR, PPDS, AtCPR, and PgUGT74A1 proteins, respectively, and a transformed cell for producing F2 including the expression vector or a fragment thereof.

The transformed cell may be a yeast, but is not limited thereto.

In another aspect, the present invention provides an expression vector, which further includes polynucleotides encoding dammarenediol-II synthase (DS), truncated HMG-CoA reductase (tHMGR), protopanaxadiol synthase (PPDS), *Arabidopsis thaliana* cytochrome p450 reductase (AtCPR), panax ginseng UDP glycosyltransferase 74A1 (PgUGT74A1), and panax ginseng UDP glycosyltransferase 94B1 (PgUGT94B1) proteins, respectively, in addition to the expression vector including the polynucleotide encoding the UDP glycosyltransferase protein; and a transformed cell for producing Rd including the expression vector or a fragment thereof.

The dammarenediol-II synthase (DS), truncated HMG-CoA reductase (tHMGR), protopanaxadiol synthase (PPDS), *Arabidopsis thaliana* cytochrome p450 reductase (AtCPR), and panax ginseng UDP glycosyltransferase 74A1 (PgUGT74A1) are the same as described above.

The UDP glycosyltransferase protein, the expression vector, and the transformed cell are the same as described above.

Panax ginseng UDP glycosyltransferase 94B1 (PgUGT94B1) is a UDP glycosyltransferase acting specifically on $Rh_e$ and F2, which are PPD-type ginsenosides, to cause β-1,2 glycosylation of O-glucoside located at C-3 position thereby converting $Rh_2$ and F2, which are ginsenosides, into $Rg_3$ and Rd, respectively. The PgUGT94B 1 may be defined by an amino acid sequence in KR Pat. No. 10-1479608. Any protein variants having a deletion, a modification, a substitution, or an addition in part of their amino acid sequences therein may be included without limitation within the scope of the present invention, as long as the PgUGT94B 1 variant has an amino acid sequence having similarity of 70% or higher, preferably 80% or higher, more preferably 90% or higher, even more preferably 95% or higher, even much more preferably 98% or higher, and most preferably 99% or higher, to the amino acid sequence described in KR Pat. No. 10-1479608, which has a biological activity substantially the same as or corresponding to that of the PgUGT94B1.

The polynucleotide encoding the PgUGT94B1 protein may be preferably a polynucleotide defined by the nucleotide sequence described in KR Pat. No. 10-1479608. Any polynucleotide variants having a deletion, a modification, a substitution, or an addition in part of their nucleotide sequences therein may be included without limitation within the scope of the present invention, as long as the variant has an nucleotide sequence having similarity of 70% or higher, preferably 80% or higher, more preferably 90% or higher, even more preferably 95% or higher, and even much more preferably 98% or higher, to the nucleotide sequence described in KR Pat. No. 10-1479608, which encodes a protein having a biological activity substantially the same as that of the PgUGT94B1 protein.

In an exemplary embodiment of the present invention, *S. cerevisiae* Rd strain having a biosynthesis pathway of ginsenoside Rd was constructed by simultaneously introducing pRS424 DS, pRS426 tHMG1, pRS425 PPD containing PPDS and AtCPR, pRS423 Rd containing PgUGT74A1, PgUGT94B1, and PgUGT71A1 into *S. cerevisiae* MET3p-ERG7 via lithium acetate method (FIG. 12), and the *S. cerevisiae* Rd strain was cultured via fed-batch fermentation for 10 d (OD600≈80) in the presence of methionine. Additionally, yeast cells were harvested by centrifugation and disrupted by sonication. Ginsenosides were extracted using BtOH and then evaporated BtOH. Finally, ginsenoside Rd was re-extracted by MtOH and the extracted ginsenoside was analyzed by HPLC and LC-MS/MS. As a result, the yeast harboring PgUGT74A1, PgUGT94B1, and PgUGT71A1 produced a new peak at 5.88 min, which is identical to the retention time of Rd in HPLC((A) of FIG. 13), whereas the observed retention time of products in LC-MS/MS detected by MRM was 5.93 min with the transition at 969.5→789.5 ((B) of FIG. 13). These results indicate that the PgUGT74A1, PgUGT94B1, and PgUGT71A1 enable the de novo production of ginsenoside Rd through yeast fermentation.

Mode for the Invention

The present invention is described in detail through examples. However, the following examples are for illustrative purpose only, and the scope of the present invention is not limited by the examples.

EXAMPLE 1

Cloning and Purification of Ginseng UDP Glycosyltransferase PgUGT71A1

From ginseng cDNAs, genes were amplified by PCR using PgUGT71A1-F (5'-AGGCAGGATCCAT-GAAGTCAGAATTGATATTCTTGCCCGCCCCGGC-3'; SEQ ID NO: 17) and PgUGT71A1-R (5'-AGGCATCTC-GAGTCACATAAATTTTCTCAAATAGTTTGGCCAAT-GAAT-3'; SEQ ID NO: 18) primers and polymerases, and the terminals of the genes were digested with the restriction enzymes BamHI and XhoI. Then, the genes were cloned into a pGEX-4T1 vector to construct an expression vector, which was transformed into the *E. coli* BL21 (DE3)-RIL strain to obtain a PgUGT71A1-expressing strain.

After inducing the strain to express proteins with IPTG, the resulting protein was purified using sepharose-4B resin to obtain the PgUGT71A1 enzyme.

EXAMPLE 2

In-vitro Enzyme Assay

A glycosyltransferase assay was conducted in a reaction buffer (10 mM PBS buffer, pH 7) containing the purified PgUGT71A1 (30 μg), a ginsenoside compound (5 mM) and UDP-glucose (50 mM). For this assay, 4 different types of ginsenosides, i.e., protopanaxadiol (PPD), protopanaxatriol (PPT), Rh$_2$ and Rg$_3$, were caused to react the enzyme of the present disclosure. The structures of the ginsenosides are shown in FIG. 1.

The reaction mixture was incubated at 35° C. for 12 hours and the resulting products were analyzed by thin-layer chromatography (TLC) or high-performance liquid chromatography (HPLC).

The TLC analysis was performed using a mobile phase (acetone:methanol:DDW=65:35:10 vol/vol) and a 60F254 silica gel plate (Merck, Germany). The resolved product on the TLC plate was detected by spraying 10% (vol/vol) sulfuric acid (H2SO4) and heating at 110° C. for 5 minutes.

The HPLC analysis was performed using an ODS(2) C18 column (Phenomenex, USA). The condition of gradient application of water and acetonitrile was as follows: flow rate=1 mL/min, 0 minute, 68% water and 32% acetonitrile; 8 minutes, 35% water and 65% acetonitrile; 12 minutes, 0% water and 100% acetonitrile; 20 minutes, 0% water and 100% acetonitrile; 20.1 minutes, 68% water and 32% acetonitrile; and 28 minutes, 68% water and 32% acetonitrile.

The ginsenosides were detected by monitoring at a wavelength of 203 nm using a UV detector (Agilent, USA).

EXAMPLE 3

RNA Isolation and Real-time PCR Analysis

Total RNA was isolated from the leaf or root of 15-month-old ginseng using the Spectrum Plant Total RNA kit (Sigma-Aldrich). 200 μM methyl jasmonate (MeJA) was sprayed onto the leaves of ginseng every day for a total of 5 days and samples were collected on the 6th day. 1 μg of the total RNA was used for cDNA synthesis.

The expression level of different genes was examined by quantitative RT-PCR using the primer sets listed in Table 1, and the result was normalized to the expression level of tubulin.

TABLE 1

| Gene | Sequence(5'->3') | SEQ ID NO |
|---|---|---|
| PgDS | 5'-AAATGAAGAAGGTGGTTGGG-3' | 3 |
|  | 5'-CTCTATGCAGAGGTGTCGGA-3' | 4 |
| PgPPDS | 5'-GGGAGGATTTGAGGAAGATGAAG-3' | 5 |
|  | 5'-CAGATGCATCTTCCATCCCTTTGG-3' | 6 |
| PgPPTS | 5'-GAGATTAGTACCTCCTTCTCAAGG-3' | 7 |
|  | 5'-GAATGGCATAGGTCCATCTCCTTC-3' | 8 |
| PgUGT74A1 | 5'-TATCGAACCCGAACGTACAA-3' | 9 |
|  | 5'-GTCGAGTTCCAACCACAATG-3' | 10 |
| PgUGT94B1 | 5'-GACAGAGGATTGGTTGTGGA-3' | 11 |
|  | 5'-TCAAAGGCTGATCAAGATGC-3' | 12 |
| PgUGT71A1 | 5'-CCTCCGGATGGATAGTATGATCC-3' | 13 |
|  | 5'-CATTGCAATCTCCTTCACCTGG-3' | 14 |
| PgTubulin | 5'-GAAGGCTTTCTTGCATTGGT-3' | 15 |
|  | 5'-CCCAGATCGTCTTCTTCTCC-3' | 16 |

EXAMPLE 4

NGS Analysis

RNA was extracted from the leaf and root of ginseng which had been treated and not treated with MeJA, and a cDNA library was constructed from 1 μg of the total RNA using the TruSeq RNA library kit. Following polyA-selected RNA extraction, RNA fragmentation and random hexamer-primed reverse transcription, 100 nt paired-end sequencing was conducted using Illumina HiSeq2000.

The resulting sequences were subjected to de novo transcriptome assembly using the Trinity (2011-11-26 version) program. The produced contigs (transcripts) were analyzed using Blast (version 2.2.25+). The GO database (released on 20-04-2012) and the NR database of NCBI (download date: 2012/05/07) were used. To determine the expression level of the assembled contigs (transcripts), Bowtie (version 0.12.8) was used as a mapping program. The expression level was expressed as fragments per kilobase of exon per million fragments mapped (FPKM) with a program released by the Trinity group using the RSEM algorithm.

EXAMPLE 5

Production of Ginsenosides in Yeast

EXAMPLE 5-1

Construction of ERG7 Down Regulation Cassette

In order to construct the ERG7 down regulation strain (S. cereivisae MET3p-ERG7), ERG7 down regulation cassette was constructed. For the ERG7 down regulation cassette carrying MET3 promoter, ERG7 gene, and CYC1 terminator, pRS306 plasmid was used as a platform. To suppress ERG7 gene, MET3 promoter (MET3p), which is capable of suppressing transcription level by supply of methionine, was chosen. MET3p was amplified from genomic DNA of S. cerevisiae CEN.PK 2-1D by PCR amplification with the following primer set: MET3p for pRS306-F (SacI) and MET3p for pRS306-B (XbaI) (Table 2).

TABLE 2

| Primer | Sequence(5'->3') | SEQ ID NO |
|---|---|---|
| MET3p(pRS306-F (SacI)) | 5'-AGGCATGAGCTCTTTAGTACTAACAGA-GACTTTTGTCACAACTACA TATAAGTG-TACAAATA-3' | 19 |
| MET3p(pRS306-B (XbaI)) | 5'-AGGCATTCTAGATGTTAATTATACTTT-TATTCTTGTTATTATTATACTTTCT TAGTTCCTTTT-3' | 20 |

ERG7 was amplified from genomic DNA of S. cerevisiae CEN.PK 2-1D by PCR amplification with the following primer set: ERG7 for pRS306-F (SpeI) and ERG7 for pRS306-B (XhoI) (Table 3).

TABLE 3

| Primer | Sequence(5'->3') | SEQ ID NO |
|---|---|---|
| ERG7(pRS306-F(SpeI)) | 5'-AGGCATACTAGTATGACAGAATTTTATTCTG ACACAATCGGTCT-3' | 21 |
| ERG7(pRS306-B(XhoI)) | 5'-AGGCATCTCGAGTTAAAGCGTATGTGTTTCA TATGCCCTGCTGT-3' | 22 |

CYC1 terminator was amplified from pRS424-GPD plasmid by PCR amplification with the following primer set:

CYC1 terminator for pRS306-F (XhoI) and CYC1 terminator for pRS306-B (KpnI) (Table 4).

TABLE 4

| Primer | Sequence(5'->3') | SEQ ID NO |
|---|---|---|
| CYC1ter (pRS306-F (XhoI)) | 5'-AGGCATCTCGAGTCATGTAATTAGTTATGTC ACGCTTACATTCA CGCCCTC-3' | 23 |
| CYC1ter (pRS306-B (KpnI)) | 5'-AGGCATGGTACCGGCCGCAAATTAAAGCCT TCGAGCGTCCCAAAA CC-3' | 24 |

Each fragment was inserted into the pRS306 vector and thereby constructed a platform plasmid called pRS3063p-MET3p-ERG7-CYC1ter ((A) of FIG. 5).

ERG7 down regulation cassette was constructed via PCR using the pRS3063p-MET3p-ERG7-CYC1ter plasmid as a template. The ERG7 down regulation cassette includes URA3 gene and MET3p-ERG6-CYC1ter as markers. The cassette from URA3 region to CYC1 terminator was amplified by PCR with ERG7 knock down-F and ERG7 knock down-B primers(Table 5) which include homologous arms ((B) of FIG. 5).

TABLE 5

| Primer | Sequence(5'->3') | SEQ ID NO |
|---|---|---|
| ERG7 knock down-F | 5'-GCCCAATAACCTTACCAATAATCGTCGCCCAC AAAGAAAGTAC AAAACAGTCAGAGCAGATTG-TACTGAGAGTGCACCACGCTTT-3' | 25 |
| ERG7 knock down-B | 5'-TGCACTAGTTTCTAATTGTTGCAGCCTCTAA-CAACACTTATAAATAAAACTCGGAATTAACCCT CACTAAAGGGAACAAAAGCTG-3' | 26 |

EXAMPLE 5-2

Construction of *S. Cerevisiae* MET3p-ERG7 Strain and Confirmation of ERG7 Down Regulation The constructed ERG7 down regulation cassette was integrated into *S. cerevisiae* CEN.PK 2-1D genome by lithium acetate method (transformation of yeast by lithium acetate, single-stranded carrier DNA, polyethylene glycol method). Transformants were selected on SD-Leu-Trp-His plates. The selected transformans were incubated in 5 ml YPD media for genomic DNA isolation for confirmation of cassette integration by PCR amplification with ERG7 knock down confirm-F and ERG7 knock down confirm-B primers (Table 6). After the replacement, yeast was selected on 5-FOA (5-Fluoroorotic acid) plate to recover URA3 marker and the resulting yeast was used for further analysis.

TABLE 6

| Primer | Sequence(5'->3') | SEQ ID NO |
|---|---|---|
| ERG7 knock down confirm-F | 5'-GCCCAATAACCTTAC-CAATAATCGTCGCCCACAAAGAAGTA CAAA ACAG-3' | 27 |

TABLE 6-continued

| Primer | Sequence(5'->3') | SEQ ID NO |
|---|---|---|
| ERG7 knock down confirm-B | 5'-TGCACTAGTTTCTAATTGTTGCAGC-CTCTAACAACACTTATAAATAAA AC-3' | 28 |

For the confirmation of accumulation of 2,3-oxidosqualene, flask cultivation was performed and metabolites were analyzed by HPLC. Seed cultures for flask cultivation were prepared by inoculating 1 mL of frozen cells in 15% (v/v) glycerol into a 250 mL flask containing 50 mL of SD-TRP-LEU-HIS-URA medium. For flask cultivation, seed cultures were grown for 2 days at 30° C. with an OD 600 of 4~7.20 mL of seed cultures were inoculated into 1 L of batch medium (2% v/v) in 2L flasks. The cultured cells were harvested and refluxed with 20 mL of 20% KOH/50% EtOH solution aq. for 1 hour. After extraction with the same volume of hexane, the extract was evaporated and re-extracted using 1.5 mL of acetone. The extract was analyzed by HPLC analysis. HPLC analysis was performed using an ODS(2) C18 column (Phenomenex, Calif., USA) at a flow rate of 1 mL/min as isocratic method with 100% acetonitrile. The metabolites (squalene, 2,3-oxidosqualene) were monitored at a wavelength of 203 nm with a UV-detector (Agilent Technologies, CA, USA).

EXAMPLE 5-3

De Novo Synthesis of Ginsenoside in *S. Cerevisiae*

De novo synthesis of ginsenoside was examined by culturing *S. cerevisiae* harboring ginsenoside biosynthetic genes in a bioreactor. A defined medium, described by van Hoek et al., containing methionine was used for the fermentation (van Hoek, de Hulster et al. 2000; Lenihan, Tsuruta et al. 2008; Westfall, Pitera et al. 2012). The batch culture medium contained 20 g/L of glucose, 15 g/L of $(NH_4)_2SO_4$, 8 g/L of $KH_2PO_4$, 0.72 g/L of $ZnSO_4 \cdot 7H_2O$, 6.15 g/L of $MgSO_4 \cdot 7H_2O$, 12 mL/L of a vitamin solution, 0.3 g/L of methionine, and 10 mL/L of a trace metal solution. The trace metal solution for the medium contained 15 g/L of EDTA, 10.2 g/L of $ZnSO_4 \cdot 7H_2O$, 0.50 g/L of $MnCl_2 \cdot 4H_2O$, 0.5 g/L of anhydrous $CuSO_4$, 0.86 g/L of $CoCl_2 \cdot 6H_2O$, 0.56 g/L of $Na_2MoO_4 \cdot 2H_2O$, 3.84 g/L of $CaCl_2 \cdot 2H_2O$, and 5.12 g/L of $FeSO_4 \cdot 7H_2O$. The vitamin solution contained 0.05 g/L of biotin, 1 g/L of calcium pantothenate, 1 g/L of nicotinic acid, 25 g/L of myoinositol, 1 g/L of thiamine HCL, 1 g/L of pyridoxol HCl, and 0.2 g/L of 4-aminobenzoicacid. The feeding solution contained 578 g/L of glucose, 9 g/L of KH2PO4, 3.5 g/L of K2SO4, 0.28 g/L of Na2SO4, 5.12 g/L of MgSO4?7H2O, and 1 g/L of methionine. Fed-batch fermentation was performed in a 1.5-LBioreactor (Biotron, Korea) at 30° C. with air flow of 1 L/min and 400 rpm agitation. The pH-stat feeding strategy was used for fed-batch fermentation by feeding glucose(>pH5.51) and by adding 5% $NH_4OH$(<pH5.4).

For the analysis of de novo synthesized ginsenosides, 50 ml of cells were harvested by centrifugation (10 min, 2898 Xg), resuspended in 20 mL of DDW, and disrupted by sonication (Vibra-cell; Sonics & Materials, CT, USA). Metabolites were extracted with 50% methanol (v/v), purified on a SEP-PAK 18 cartridge, and analyzed via HPLC and LC-MS/MS.

EXAMPLE 5-4

HPLC Analysis and LC-ESI-MS/MS Analysis of Ginsenosides

HPLC analyses were performed using an ODS(2) C18 column (Phenomenex, Calif., USA) at a flow rate of 1 mL/min as follows: 0 min, 68% water and 32% acetonitrile; 8 min, 35% water and 65% acetonitrile; 12 min, 0% water and 100% acetonitrile; 20 min, 0% water and 100% acetonitrile; 20.1 min, 68% water, and 32% acetonitrile; and 28 min, 68% water and 32% acetonitrile. Ginsenosides were monitored at a wavelength of 203 nm with a UV-detector (Agilent Technologies, CA, USA).

Identification of each ginsenoside was performed using an HPLC-MS/MS system composed of an HPLC System (HP1100; Agilent Technologies), a triple-quadrupole tandem mass spectrometer (API-2000; Applied Biosystems, CA, USA) equipped with an autosampler, a heated electrospray ionization source (H-ESI), a triple-stage quadrupole mass analyzer, and Analyst 1.4 software for data acquisition. A reversed-phase column (Fortis H2o C18, 2.1×100 mm, 3-mm pore size; Fortis Technologies Ltd., UK) was used for sample separation. The mobile phase for chromatographic separation consisted of 0.01% acetic acid aqueous water (A), and 0.01% acetic acid aqueous acetonitrile (B). The gradient elution program, with a constant flow rate of 250 μL/min, was as follows: 0 min, 68% A and 32% B; 3 min, 45% A and 55% B; 8 min, 40% A and 60% B; 13 min, 20% A and 80% B; 18 min, 0% A and 100% B; 22 min, 0% A and 100% B; 22.1 min, 68% A and 32% B; 30 min, 68% A and 32% B. The column temperature was set at 25° C. To detect ginsenoside compounds (PPD, $Rh_2$, $Rg_3$, C—K, F2, and Rd), the multiple reaction monitoring (MRM) method was used. The transitions were set at m/z 461.1→425.5 for PPD, at m/z 645.3→23.2 for $Rh_2$, at m/z 807.4→365.3 for $Rg_3$, at m/z 645.4→23.2 for C—K, m/z 807.5→627.5 for F2, and at m/z 969.3→789.4 for Rd, respectively. For full-scan MS analyses, spectra were recorded in the m/z range from 400 to 1,000 according to the transition pattern (Kim, Cui et al. 2012). The MS/MS conditions were optimized by introducing a standard solution of analyte via a syringe pump at 10 μL/min. The ES-MS parameters were as follows: ionspray voltage, 4,200 V; ion source gas 1, 20; curtain gas, 20; and collision gas, 2.

TEST EXAMPLE 1

Specific Glycosyltransferase Activity for Hydroxyl Group at C-20 Position of PPD-type and PPT-type Ginsenosides of PgUGT71A1

The substrate specificity and regioselectivity of the PgUGT71A1 identified in Example 1 were investigated as follows.

First, the recombinant PgUGT of Example 1, PgUGT71A1, was incubated with 9 different types of ginsenosides (PPD, $Rh_2$, $Rg_3$, C—K, F2, Rd, PPT, F1, and $Rh_1$) in the presence of UDP-glucose. It was confirmed by thin-layer chromatography (TLC) that reaction occurred for PPD, $Rh_2$, $Rg_3$ and PPT.

In order to confirm the result again, 4 different types of ginsenosides (PPD, PPT, $Rh_2$, and $Rg_3$) were incubated with PgUGT71A1, and the products converted by the recombinant PgUGT71A1 were analyzed by TLC. The result is shown at the top of FIG. 2. The result was confirmed by comparing the locations of the migrating spots with those of PPD, PPT, $Rh_2$, $Rg_3$, C—K, F2, Rd, and F1 used as standard samples.

As a result, it was confirmed that PgUGT71A1 converted PPD to compound K (C—K), $Rg_3$ to Rd, $Rh_2$ to F2, and PPT to F1 (FIG. 2, top).

The result was further confirmed by HPLC, as shown at the bottom of FIG. 2.

As in the TLC analysis result, it was confirmed that PgUGT71A1 converted PPD to C—K, $Rg_3$ to Rd, $Rh_2$ to F2, and PPT to F1 (FIG. 2, bottom).

Overall, the above results demonstrate that PgUGT71A1 is an enzyme having an activity of transferring UDP-glucose to a hydroxyl group at the C20-position of PPD-type and PPT-type ginsenosides, particularly a PPD-type ginsenoside and a PPT-type ginsenoside not having a sugar at the C-6 position.

TEST EXAMPLE 2

Enhancement of PgUGT71A1 Expression by Methyl Jasmonate (MeJA)

It was investigated whether PgUGT71A1 of the present invention is mainly expressed in the root of ginseng that has been traditionally used for medicinal purposes. Also, the organ-specific expression patterns of PgUGT71A1 of the present invention were examined along with 3 different ginsenoside biosynthetic genes dammarenediol-II synthase (PgDS), protopanaxadiol synthase (PgPPDS), and protopanaxatriol synthase (PgPPTS).

Methyl jasmonate (MeJA) is known to enhance the expression of the biosynthetic genes of ginseng in hairy root cultures. Based on this fact, it was examined whether the expression of PgUGT71A1, i.e., the UDP glycosyltransferase of the present invention, can be increased by MeJA. For this, 15-month-old ginseng grown in a growth chamber under LD conditions was used. MeJA was sprayed onto the leaves of the ginseng every day for a total of 5 days and samples were collected on the 6th day in order to analyze the expression level of the ginsenoside biosynthetic genes.

As a result, all the ginsenoside biosynthetic genes were expressed in both leaves and roots of ginseng, and the expression of the PgUGT71A1 of the present invention was significantly enhanced by the MeJA treatment (FIGS. 3 and 4).

Overall, the above results demonstrate that the PgUGT71A1 of the present invention is a protein involved in the biosynthesis of ginseng. In addition, since MeJA enhances the expression of the PgUGT71A1, which is the glycosyltransferase of the present invention, it can be seen that MeJA may be used to enhance the expression of PgUGT71A1.

TEST EXAMPLE 3

PgUGT71A1 Enabling the De Novo Synthesis of C—K in Yeast

In order to produce compound K (C—K), pRS424-DS, pRS426-tHMG1, pRS425-PPD containing PPDS and AtCPR, and pRS423-C—K containing PgUGT71A1 were introduced into *S. cerevisiae* MET3p-ERG7, and *S. cerevisiae* C—K strain having a biosynthetic pathway of C—K was constructed (FIG. 6).

To determine whether ginsenosides C—K could be produced de novo in yeast, *S. cerevisiae* C—K strain was grown via fed-batch fermentation for 10 d (OD600≈80) in the presence of methionine. The yeast cells were harvested by centrifugation and disrupted by sonication. Ginsenosides were extracted using MtOH and purified using Sep-PAK. The purified ginsenosides were analyzed by HPLC and LC-MS/MS. Yeast harboring PgUGT71A1 produced a new peak at 11.97 min which is identical to the retention time of C—K in HPLC ((A) of FIG. 7). The observed retention time of products in LC-MS/MS detected by MRM was 11.46 min with the transition at 645.4→23.2, which is identical to C—K ((B) of FIG. 7). These results indicate that the PgUGT71A1 enables the de novo production of ginsenoside through yeast fermentation (4.5 mg/L).

TEST EXAMPLE 4

PgUGT71A1 and PgPPTS Enable the De Novo Synthesis of Ginsenosides F1 in Yeast

In order to produce ginsenoside F1, pRS424-DS, pRS426-tHMG1, pRS425-PPD containing PPDS and AtCPR, and pRS423-F1 containing PgUGT71A1 and PgPPTS were introduced into S. cerevisiae MET3p-ERG7, and S. cerevisiae F1 strain having a biosynthetic pathway of ginsenoside F1 was constructed (FIG. 8).

To determine whether ginsenosides F1 could be produced de novo in yeast, S. cerevisiae F1 strain was grown via fed-batch fermentation for 10 d (OD600≈80) in the presence of methionine. Yeast cells were harvested by centrifugation and disrupted by sonication. Ginsenosides were extracted using BtOH and then BtOH was evaporated. Finally, ginsenoside F1 was re-extracted using MtOH. Extracted ginsenosides were analyzed by HPLC and LC-MS/MS. Yeast harboring PgUGT71A1 and PgPPTS produced a new peak at 6.01 min which is identical to the retention time of ginsenoside F1 in HPLC ((A) of FIG. 9). The observed retention time of products in LC-MS/MS detected by MRM was 6.13 min with the transition at 661.5→203, which is identical to ginsenoside F1 ((B) of FIG. 9). These results indicate that the PgUGT71A1 and PgPPTS enable the de novo production of ginsenoside through yeast fermentation.

TEST EXAMPLE 5

PgUGT74A1 and PgUGT71A1 Enable the De Novo Synthesis of Ginsenoside F2 in Yeast

In order to produce ginsenoside F2, pRS424-DS, pRS426-tHMG1, pRS425-PPD containing PPDS and AtCPR, and pRS423-F2 containing PgUGT74A1 and PgUGT71A1 were introduced into S. cerevisiae MET3p-ERG7, and S. cerevisiae F2 strain having a biosynthetic pathway of ginsenoside F2 was constructed (FIG. 10).

To determine whether ginsenosides F2 could be produced de novo in yeast, S. cerevisiae F2 strain was grown via fed-batch fermentation for 10 d (OD600≈80) in the presence of methionine. The yeast cells were harvested by centrifugation and disrupted by sonication. Ginsenosides were extracted using BtOH and then BtOH was evaporated. Finally, ginsenoside F2 was re-extracted using MtOH. The extracted ginsenosides were analyzed by HPLC and LC-MS/MS. The yeast harboring PgUGT74A1 and PgUGT71A1 produced a new peak at 7.81 min which is identical to the retention time of ginsenoside F2 in HPLC ((A) of FIG. 11). The observed retention time of products in LC-MS/MS detected by MRM was 7.35 min with the transition at 807.5→627.5, which is identical to ginsenoside F2 ((B) of FIG. 11). These results indicate that PgUGT74A1 and PgUGT71A1 enable the de novo production of ginsenoside through yeast fermentation.

TEST EXAMPLE 6

PgUGT74A1, PgUGT94B1 and PgUGT71A1 Enable the De Novo Synthesis of Ginsenoside Rd In order to produce ginsenoside Rd, pRS424-DS, pRS426-tHMG1, pRS425-PPD containing PPDS and AtCPR, and pRS423-Rd containing PgUGT74A1, PgUGT94B1 and PgUGT71A1 were introduced into S. cerevisiae MET3p-ERG7, and S. cerevisiae Rd strain having a biosynthetic pathway of ginsenoside Rd was constructed (FIG. 12).

To determine whether ginsenosides Rd could be produced de novo in yeast, S. cerevisiae Rd strain was grown via fed-batch fermentation for 10 d (OD600≈80) in the presence of methionine. The yeast cells were harvested by centrifugation and disrupted by sonication. Ginsenosides were extracted using BtOH and then BtOH was evaporated. Finally, ginsenoside Rd was re-extracted using MtOH. The extracted ginsenosides were analyzed by HPLC and LC-MS/MS. The yeast harboring PgUGT74A1, PgUGT94B1, and PgUGT71A1 produced a new peak at 5.88 min which is identical to the retention time of ginsenoside Rd in HPLC ((A) of FIG. 13). The observed retention time of products in LC-MS/MS detected by MRM was 5.93 min with the transition at 969.5→789.5, which is identical to ginsenoside Rd ((B) of FIG. 13). These results indicate that PgUGT74A1, PgUGT94B1 and PgUGT71A1 enable the de novo production of ginsenoside through yeast fermentation.

It will be apparent to those of ordinary skill in the art to which the present invention belongs that various modifications and changes may be made without departing from the scope and spirit of the disclosure. Therefore, it should be understood that the above-described exemplary embodiments are not limitative, but illustrative in all aspects. The scope of the present invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A method for preparing a protopanaxadiol (PPD)- or protopanaxatriol (PPT)-type ginsenoside whose hydroxyl group at the C-20 position is glycosylated, comprising:

contacting a uridine diphosphate (UDP) glycosyltransferase protein with a PPD- or PPT-type ginsenoside having a hydroxyl group at the C-20 position to produce a glycosylated PPD- or PPT-type ginsenoside, wherein the UDP glycosyltransferase protein is defined by the amino acid sequence of SEQ ID NO:1.

2. The method according to claim 1, wherein the PPD- or PPT-type ginsenoside having the hydroxyl group at the C-20 position is one or more selected from the group consisting of PPD, Rh2, Rg3, and PPT.

3. The method according to claim 1, wherein the method comprises one or more conversion step selected from the group consisting of a conversion of PPD to compound K (C—K), a conversion of Rh2 to F2, a conversion of Rg3 to Rd, and a conversion of PPT to F1.

* * * * *

SEQUENCE LISTING

<160> NUMBER OF SEQ ID NOS: 41

<210> SEQ ID NO 1
<211> LENGTH: 475
<212> TYPE: PRT
<213> ORGANISM: Panax ginseng

<400> SEQUENCE: 1

```
Met Lys Ser Glu Leu Ile Phe Leu Pro Ala Pro Ala Ile Gly His Leu
1               5                   10                  15

Val Gly Met Val Glu Met Ala Lys Leu Phe Ile Ser Arg His Glu Asn
            20                  25                  30

Leu Ser Val Thr Val Leu Ile Ala Lys Phe Tyr Met Asp Thr Gly Val
        35                  40                  45

Asp Asn Tyr Asn Lys Ser Leu Leu Thr Asn Pro Thr Pro Arg Leu Thr
    50                  55                  60

Ile Val Asn Leu Pro Glu Thr Asp Pro Gln Asn Tyr Met Leu Lys Pro
65                  70                  75                  80

Arg His Ala Ile Phe Pro Ser Val Ile Glu Thr Gln Lys Thr His Val
                85                  90                  95

Arg Asp Ile Ile Ser Gly Met Thr Gln Ser Glu Ser Thr Arg Val Val
            100                 105                 110

Gly Leu Leu Ala Asp Leu Leu Phe Ile Asn Ile Met Asp Ile Ala Asn
        115                 120                 125

Glu Phe Asn Val Pro Thr Tyr Val Tyr Ser Pro Ala Gly Ala Gly His
    130                 135                 140

Leu Gly Leu Ala Phe His Leu Gln Thr Leu Asn Asp Lys Lys Gln Asp
145                 150                 155                 160

Val Thr Glu Phe Arg Asn Ser Asp Thr Glu Leu Leu Val Pro Ser Phe
                165                 170                 175

Ala Asn Pro Val Pro Ala Glu Val Leu Pro Ser Met Tyr Val Asp Lys
            180                 185                 190

Glu Gly Gly Tyr Asp Tyr Leu Phe Ser Leu Phe Arg Arg Cys Arg Glu
        195                 200                 205

Ser Lys Ala Ile Ile Asn Thr Phe Glu Glu Leu Glu Pro Tyr Ala
    210                 215                 220

Ile Asn Ser Leu Arg Met Asp Ser Met Ile Pro Pro Ile Tyr Pro Val
225                 230                 235                 240

Gly Pro Ile Leu Asn Leu Asn Gly Asp Gly Gln Asn Ser Asp Glu Ala
                245                 250                 255

Ala Val Ile Leu Gly Trp Leu Asp Asp Gln Pro Pro Ser Ser Val Val
            260                 265                 270

Phe Leu Cys Phe Gly Ser Tyr Gly Thr Phe Gln Glu Asn Gln Val Lys
        275                 280                 285

Glu Ile Ala Met Gly Leu Glu Arg Ser Gly His Arg Phe Leu Trp Ser
    290                 295                 300

Leu Arg Pro Ser Ile Pro Lys Gly Glu Thr Lys Leu Gln Leu Lys Tyr
305                 310                 315                 320

Ser Asn Leu Glu Glu Ile Leu Pro Val Gly Phe Leu Asp Arg Thr Ser
                325                 330                 335

Cys Val Gly Lys Val Ile Gly Trp Ala Pro Gln Val Ala Val Leu Gly
            340                 345                 350

His Glu Ala Val Gly Gly Phe Leu Ser His Cys Gly Trp Asn Ser Thr
        355                 360                 365

Leu Glu Ser Val Trp Cys Gly Val Pro Val Ala Thr Trp Pro Met Tyr
    370                 375                 380

Gly Glu Gln Gln Leu Asn Ala Phe Glu Met Val Lys Glu Leu Gly Ile
385                 390                 395                 400

Ala Val Glu Ile Glu Val Asp Tyr Lys Asn Glu Tyr Phe Asn Met Asn
                405                 410                 415
```

Asn Asp Phe Ile Val Arg Ala Glu Glu Ile Glu Thr Lys Ile Lys Lys
            420                 425                 430

Leu Met Met Asp Glu Lys Asn Ser Glu Ile Arg Lys Lys Val Lys Glu
            435                 440                 445

Met Lys Glu Lys Ser Arg Leu Ala Met Ser Glu Asn Gly Ser Ser Tyr
450                 455                 460

Asn Ser Leu Ala Lys Leu Phe Glu Lys Ile Met
465                 470                 475

<210> SEQ ID NO 2
<211> LENGTH: 1428
<212> TYPE: DNA
<213> ORGANISM: Panax ginseng

<400> SEQUENCE: 2

```
atgaagtcag aattgatatt cttgcccgcc ccggccatcg acacctcgt gggaatggtg      60
gagatggcta aactcttcat cagtcgacat gaaaacctct cggtcaccgt cctcatcgcg     120
aaattctaca tggatacggg ggtagacaac tacaataaat cactcttaac aaaccctacc    180
ccgcgtctca caattgtaaa tctcccggaa accgaccccc aaaactatat gctcaaacca    240
cgccatgcca tctttcctag cgtcatcgag actcagaaga cacacgtgcg agacataata    300
tcaggcatga ctcagtccga gtcgactcgg gtcgttggtt tgctggctga ccttttgttc    360
atcaacatta tggacattgc caatgagttc aatgttccaa cttatgtata ctcccctgcc    420
ggagccggtc atcttggcct cgcgttccat ctccagacac tcaacgacaa aaagcaagat    480
gtgaccgagt tcaggaactc ggacactgag ttattggtac cgagttttgc aaacccggtt    540
cccgccgagg tcttgccgtc gatgtatgtg ataaagaag gtgggtatga ttatttgttt    600
tcattgttcc ggaggtgcag agagtcaaag gcaattatta ttaacacgtt tgaggagctg    660
gaacccatg cgatcaattc cctccggatg gatagtatga tccctccgat ctacccggtg    720
ggacccatac taaatctcaa cggtgatggc caaaactccg atgaggctgc tgtgatcctt    780
ggttggttag atgatcaacc accttcatct gtggtgtttt tgtgctttgg tagctatgga    840
acctttcaag aaaaccaggt gaaggagatt gcaatgggtc tagagcgcag tgggcatcgc    900
ttcttgtggt ccttgcgtcc gtctatccct aaaggcgaga caaagcttca gcttaaatac    960
tcaaatttgg aagaaattct cccagtcgga ttccttgaca ggacatcatg cgtcggaaaa   1020
gttattggat gggccccgca agtggcggtg ctcggacacg aggcagtcgg agggttcctg   1080
tctcattgtg gttggaattc gacattagag agtgtgtggt gtggcgtgcc cgtcgcaaca   1140
tggccaatgt acggcgagca acaactcaat gcttttgaga tggttaagga gttaggtatt   1200
gcggtggaaa ttgaggtgga ctataagaat gaatatttta acatgaataa tgatttatt   1260
gttagggcag aagaaatcga gacgaaaata aagaagttga tgatggatga aagaatagt   1320
gaaataagga gaaaggtaaa ggaaatgaaa gaaagagta ggcttgcaat gtctgagaat   1380
ggatcatctt ataattcatt ggccaaacta tttgagaaaa ttatgtga              1428
```

<210> SEQ ID NO 3
<211> LENGTH: 20
<212> TYPE: DNA
<213> ORGANISM: Artificial Sequence
<220> FEATURE:
<223> OTHER INFORMATION: PgDS primer

<400> SEQUENCE: 3
aaatgaagaa ggtggttggg                                                20

<210> SEQ ID NO 4
<211> LENGTH: 20
<212> TYPE: DNA
<213> ORGANISM: Artificial Sequence
<220> FEATURE:
<223> OTHER INFORMATION: PgDS primer

<400> SEQUENCE: 4
ctctatgcag aggtgtcgga                                                20

<210> SEQ ID NO 5
<211> LENGTH: 23
<212> TYPE: DNA
<213> ORGANISM: Artificial Sequence
<220> FEATURE:
<223> OTHER INFORMATION: PgPPDS primer

<400> SEQUENCE: 5
gggaggattt gaggaagatg aag                                            23

<210> SEQ ID NO 6
<211> LENGTH: 24
<212> TYPE: DNA
<213> ORGANISM: Artificial Sequence
<220> FEATURE:
<223> OTHER INFORMATION: PgPPDS primer

<400> SEQUENCE: 6
cagatgcatc ttccatccct ttgg                                           24

<210> SEQ ID NO 7
<211> LENGTH: 24
<212> TYPE: DNA
<213> ORGANISM: Artificial Sequence
<220> FEATURE:
<223> OTHER INFORMATION: PgPPTS primer

<400> SEQUENCE: 7
gagattagta cctccttctc aagg                                           24

<210> SEQ ID NO 8
<211> LENGTH: 24
<212> TYPE: DNA
<213> ORGANISM: Artificial Sequence
<220> FEATURE:
<223> OTHER INFORMATION: PgPPTS primer

<400> SEQUENCE: 8
gaatggcata ggtccatctc cttc                                           24

<210> SEQ ID NO 9
<211> LENGTH: 20
<212> TYPE: DNA
<213> ORGANISM: Artificial Sequence
<220> FEATURE:
<223> OTHER INFORMATION: PgUGT74A1 primer

<400> SEQUENCE: 9
tatcgaaccc gaacgtacaa                                                20

<210> SEQ ID NO 10
<211> LENGTH: 20
<212> TYPE: DNA
<213> ORGANISM: Artificial Sequence

```
<220> FEATURE:
<223> OTHER INFORMATION: PgUGT74A1 primer

<400> SEQUENCE: 10
gtcgagttcc aaccacaatg                                              20

<210> SEQ ID NO 11
<211> LENGTH: 20
<212> TYPE: DNA
<213> ORGANISM: Artificial Sequence
<220> FEATURE:
<223> OTHER INFORMATION: PgUGT94B1 primer

<400> SEQUENCE: 11
gacagaggat tggttgtgga                                              20

<210> SEQ ID NO 12
<211> LENGTH: 20
<212> TYPE: DNA
<213> ORGANISM: Artificial Sequence
<220> FEATURE:
<223> OTHER INFORMATION: PgUGT94B1 primer

<400> SEQUENCE: 12
tcaaaggctg atcaagatgc                                              20

<210> SEQ ID NO 13
<211> LENGTH: 23
<212> TYPE: DNA
<213> ORGANISM: Artificial Sequence
<220> FEATURE:
<223> OTHER INFORMATION: PgUGT71A1 primer

<400> SEQUENCE: 13
cctccggatg gatagtatga tcc                                          23

<210> SEQ ID NO 14
<211> LENGTH: 22
<212> TYPE: DNA
<213> ORGANISM: Artificial Sequence
<220> FEATURE:
<223> OTHER INFORMATION: PgUGT71A1 primer

<400> SEQUENCE: 14
cattgcaatc tccttcacct gg                                           22

<210> SEQ ID NO 15
<211> LENGTH: 20
<212> TYPE: DNA
<213> ORGANISM: Artificial Sequence
<220> FEATURE:
<223> OTHER INFORMATION: PgTubulin primer

<400> SEQUENCE: 15
gaaggctttc ttgcattggt                                              20

<210> SEQ ID NO 16
<211> LENGTH: 20
<212> TYPE: DNA
<213> ORGANISM: Artificial Sequence
<220> FEATURE:
<223> OTHER INFORMATION: PgTubulin primer

<400> SEQUENCE: 16
cccagatcgt cttcttctcc                                              20
```

<210> SEQ ID NO 17
<211> LENGTH: 46
<212> TYPE: DNA
<213> ORGANISM: Artificial Sequence
<220> FEATURE:
<223> OTHER INFORMATION: PgUGT71A1-F (for cloning)

<400> SEQUENCE: 17
aggcaggatc catgaagtca gaattgatat tcttgcccgc cccggc       46

<210> SEQ ID NO 18
<211> LENGTH: 47
<212> TYPE: DNA
<213> ORGANISM: Artificial Sequence
<220> FEATURE:
<223> OTHER INFORMATION: PgUGT71A1-R (for cloning)

<400> SEQUENCE: 18
aggcatctcg agtcacataa ttttctcaaa tagtttggcc aatgaat      47

<210> SEQ ID NO 19
<211> LENGTH: 62
<212> TYPE: DNA
<213> ORGANISM: Artificial Sequence
<220> FEATURE:
<223> OTHER INFORMATION: MET3p_pRS306-F primer

<400> SEQUENCE: 19
aggcatgagc tctttagtac taacagagac ttttgtcaca actacatata agtgtacaaa      60
ta                                                                    62

<210> SEQ ID NO 20
<211> LENGTH: 62
<212> TYPE: DNA
<213> ORGANISM: Artificial Sequence
<220> FEATURE:
<223> OTHER INFORMATION: MET3p_pRS306-B primer

<400> SEQUENCE: 20
aggcattcta gatgttaatt atactttatt cttgttatta ttatactttc ttagttcctt      60
tt                                                                    62

<210> SEQ ID NO 21
<211> LENGTH: 44
<212> TYPE: DNA
<213> ORGANISM: Artificial Sequence
<220> FEATURE:
<223> OTHER INFORMATION: ERG7_pRS306-F primer

<400> SEQUENCE: 21
aggcatacta gtatgacaga attttattct gacacaatcg gtct       44

<210> SEQ ID NO 22
<211> LENGTH: 44
<212> TYPE: DNA
<213> ORGANISM: Artificial Sequence
<220> FEATURE:
<223> OTHER INFORMATION: ERG7_pRS306-B primer

<400> SEQUENCE: 22
aggcatctcg agttaaagcg tatgtgtttc atatgccctg ctgt       44

<210> SEQ ID NO 23
<211> LENGTH: 51

-continued

<210> SEQ ID NO 23
<211> LENGTH: 51
<212> TYPE: DNA
<213> ORGANISM: Artificial Sequence
<220> FEATURE:
<223> OTHER INFORMATION: CYC1ter_pRS306-F primer

<400> SEQUENCE: 23
aggcatctcg agtcatgtaa ttagttatgt cacgcttaca ttcacgccct c        51

<210> SEQ ID NO 24
<211> LENGTH: 47
<212> TYPE: DNA
<213> ORGANISM: Artificial Sequence
<220> FEATURE:
<223> OTHER INFORMATION: CYC1ter_pRS306-B primer

<400> SEQUENCE: 24
aggcatggta ccggccgcaa attaaagcct tcgagcgtcc caaaacc            47

<210> SEQ ID NO 25
<211> LENGTH: 85
<212> TYPE: DNA
<213> ORGANISM: Artificial Sequence
<220> FEATURE:
<223> OTHER INFORMATION: ERG7 knock down-F primer

<400> SEQUENCE: 25
gcccaataac cttaccaata atcgtcgccc acaaagaaag tacaaaacag tcagagcaga    60
ttgtactgag agtgcaccac gcttt                                         85

<210> SEQ ID NO 26
<211> LENGTH: 85
<212> TYPE: DNA
<213> ORGANISM: Artificial Sequence
<220> FEATURE:
<223> OTHER INFORMATION: ERG7 knock down-B primer

<400> SEQUENCE: 26
tgcactagtt tctaattgtt gcagcctcta acaacactta taaataaaac tcggaattaa    60
ccctcactaa agggaacaaa agctg                                         85

<210> SEQ ID NO 27
<211> LENGTH: 50
<212> TYPE: DNA
<213> ORGANISM: Artificial Sequence
<220> FEATURE:
<223> OTHER INFORMATION: ERG7 knock down confirm-F primer

<400> SEQUENCE: 27
gcccaataac cttaccaata atcgtcgccc acaaagaaag tacaaaacag               50

<210> SEQ ID NO 28
<211> LENGTH: 50
<212> TYPE: DNA
<213> ORGANISM: Artificial Sequence
<220> FEATURE:
<223> OTHER INFORMATION: ERG7 knock down confirm-B primer

<400> SEQUENCE: 28
tgcactagtt tctaattgtt gcagcctcta acaacactta taaataaaac               50

<210> SEQ ID NO 29
<211> LENGTH: 769
<212> TYPE: PRT
<213> ORGANISM: Panax ginseng

<400> SEQUENCE: 29

| | | | | | | | | | | | | | | |
|---|---|---|---|---|---|---|---|---|---|---|---|---|---|---|
| Met | Trp | Lys | Gln | Lys | Gly | Ala | Gln | Gly | Asn | Asp | Pro | Tyr | Leu | Tyr | Ser |
| 1 | | | | 5 | | | | | 10 | | | | | 15 | |
| Thr | Asn | Asn | Phe | Val | Gly | Arg | Gln | Tyr | Trp | Glu | Phe | Gln | Pro | Asp | Ala |
| | | | 20 | | | | | 25 | | | | | 30 | | |
| Gly | Thr | Pro | Glu | Glu | Arg | Glu | Val | Glu | Lys | Ala | Arg | Lys | Asp | Tyr | |
| | | | 35 | | | | 40 | | | | | 45 | | | |
| Val | Asn | Asn | Lys | Lys | Leu | His | Gly | Ile | His | Pro | Cys | Ser | Asp | Met | Leu |
| | 50 | | | | | 55 | | | | | 60 | | | | |
| Met | Arg | Arg | Gln | Leu | Ile | Lys | Glu | Ser | Gly | Ile | Asp | Leu | Leu | Ser | Ile |
| 65 | | | | | 70 | | | | | 75 | | | | | 80 |
| Pro | Pro | Leu | Arg | Leu | Asp | Glu | Asn | Glu | Gln | Val | Asn | Tyr | Asp | Ala | Val |
| | | | | 85 | | | | | 90 | | | | | 95 | |
| Thr | Thr | Ala | Val | Lys | Lys | Ala | Leu | Arg | Leu | Asn | Arg | Ala | Ile | Gln | Ala |
| | | | 100 | | | | | 105 | | | | | 110 | | |
| His | Asp | Gly | His | Trp | Pro | Ala | Glu | Asn | Ala | Gly | Ser | Leu | Leu | Tyr | Thr |
| | | | 115 | | | | | 120 | | | | | 125 | | |
| Pro | Pro | Leu | Ile | Ile | Ala | Leu | Tyr | Ile | Ser | Gly | Thr | Ile | Asp | Thr | Ile |
| | | 130 | | | | | 135 | | | | | 140 | | | |
| Leu | Thr | Lys | Gln | His | Lys | Lys | Glu | Leu | Ile | Arg | Phe | Val | Tyr | Asn | His |
| 145 | | | | | 150 | | | | | 155 | | | | | 160 |
| Gln | Asn | Glu | Asp | Gly | Gly | Trp | Gly | Ser | Tyr | Ile | Glu | Gly | His | Ser | Thr |
| | | | | 165 | | | | | 170 | | | | | 175 | |
| Met | Ile | Gly | Ser | Val | Leu | Ser | Tyr | Val | Met | Leu | Arg | Leu | Leu | Gly | Glu |
| | | | 180 | | | | | 185 | | | | | 190 | | |
| Gly | Leu | Ala | Glu | Ser | Asp | Asp | Gly | Asn | Gly | Ala | Val | Glu | Arg | Gly | Arg |
| | | | 195 | | | | | 200 | | | | | 205 | | |
| Lys | Trp | Ile | Leu | Asp | His | Gly | Gly | Ala | Ala | Gly | Ile | Pro | Ser | Trp | Gly |
| | 210 | | | | | 215 | | | | | 220 | | | | |
| Lys | Thr | Tyr | Leu | Ala | Val | Leu | Gly | Val | Tyr | Glu | Trp | Glu | Gly | Cys | Asn |
| 225 | | | | | 230 | | | | | 235 | | | | | 240 |
| Pro | Leu | Pro | Pro | Glu | Phe | Trp | Leu | Phe | Pro | Ser | Ser | Phe | Pro | Phe | His |
| | | | | 245 | | | | | 250 | | | | | 255 | |
| Pro | Ala | Lys | Met | Trp | Ile | Tyr | Cys | Arg | Cys | Thr | Tyr | Met | Pro | Met | Ser |
| | | | 260 | | | | | 265 | | | | | 270 | | |
| Tyr | Leu | Tyr | Gly | Lys | Arg | Tyr | His | Gly | Pro | Ile | Thr | Asp | Leu | Val | Leu |
| | | | 275 | | | | | 280 | | | | | 285 | | |
| Ser | Leu | Arg | Gln | Glu | Ile | Tyr | Asn | Ile | Pro | Tyr | Glu | Gln | Ile | Lys | Trp |
| | 290 | | | | | 295 | | | | | 300 | | | | |
| Asn | Gln | Gln | Arg | His | Asn | Cys | Cys | Lys | Glu | Asp | Leu | Tyr | Tyr | Pro | His |
| 305 | | | | | 310 | | | | | 315 | | | | | 320 |
| Thr | Leu | Val | Gln | Asp | Leu | Val | Trp | Asp | Gly | Leu | His | Tyr | Phe | Ser | Glu |
| | | | | 325 | | | | | 330 | | | | | 335 | |
| Pro | Phe | Leu | Lys | Arg | Trp | Pro | Phe | Asn | Lys | Leu | Arg | Lys | Arg | Gly | Leu |
| | | | 340 | | | | | 345 | | | | | 350 | | |
| Lys | Arg | Val | Val | Glu | Leu | Met | Arg | Tyr | Gly | Ala | Thr | Glu | Thr | Arg | Phe |
| | | | 355 | | | | | 360 | | | | | 365 | | |
| Ile | Thr | Thr | Gly | Asn | Gly | Glu | Lys | Ala | Leu | Gln | Ile | Met | Ser | Trp | Trp |
| | | 370 | | | | | 375 | | | | | 380 | | | |
| Ala | Glu | Asp | Pro | Asn | Gly | Asp | Glu | Phe | Lys | His | His | Leu | Ala | Arg | Ile |
| 385 | | | | | 390 | | | | | 395 | | | | | 400 |
| Pro | Asp | Phe | Leu | Trp | Ile | Ala | Glu | Asp | Gly | Met | Thr | Val | Gln | Ser | Phe |
| | | | | 405 | | | | | 410 | | | | | 415 | |

Gly Ser Gln Leu Trp Asp Cys Ile Leu Ala Thr Gln Ala Ile Ile Ala
                420                 425                 430

Thr Asn Met Val Glu Glu Tyr Gly Asp Ser Leu Lys Lys Ala His Phe
            435                 440                 445

Phe Ile Lys Glu Ser Gln Ile Lys Glu Asn Pro Arg Gly Asp Phe Leu
450                 455                 460

Lys Met Cys Arg Gln Phe Thr Lys Gly Ala Trp Thr Phe Ser Asp Gln
465                 470                 475                 480

Asp His Gly Cys Val Val Ser Asp Cys Thr Ala Glu Ala Leu Lys Cys
                485                 490                 495

Leu Leu Leu Leu Ser Gln Met Pro Gln Asp Ile Val Gly Glu Lys Pro
                500                 505                 510

Glu Val Glu Arg Leu Tyr Glu Ala Val Asn Val Leu Leu Tyr Leu Gln
            515                 520                 525

Ser Arg Val Ser Gly Gly Phe Ala Val Trp Glu Pro Pro Val Pro Lys
530                 535                 540

Pro Tyr Leu Glu Met Leu Asn Pro Ser Glu Ile Phe Ala Asp Ile Val
545                 550                 555                 560

Val Glu Arg Glu His Ile Glu Cys Thr Ala Ser Val Ile Lys Gly Leu
                565                 570                 575

Met Ala Phe Lys Cys Leu His Pro Gly His Arg Gln Lys Glu Ile Glu
                580                 585                 590

Asp Ser Val Ala Lys Ala Ile Arg Tyr Leu Glu Arg Asn Gln Met Pro
            595                 600                 605

Asp Gly Ser Trp Tyr Gly Phe Trp Gly Ile Cys Phe Leu Tyr Gly Thr
610                 615                 620

Phe Phe Thr Leu Ser Gly Phe Ala Ser Ala Gly Arg Thr Tyr Asp Asn
625                 630                 635                 640

Ser Glu Ala Val Arg Lys Gly Val Lys Phe Phe Leu Ser Thr Gln Asn
                645                 650                 655

Glu Glu Gly Gly Trp Gly Glu Ser Leu Glu Ser Cys Pro Ser Glu Lys
                660                 665                 670

Phe Thr Pro Leu Lys Gly Asn Arg Thr Asn Leu Val Gln Thr Ser Trp
            675                 680                 685

Ala Met Leu Gly Leu Met Phe Gly Gly Gln Ala Glu Arg Asp Pro Thr
690                 695                 700

Pro Leu His Arg Ala Ala Lys Leu Leu Ile Asn Ala Gln Met Asp Asn
705                 710                 715                 720

Gly Asp Phe Pro Gln Gln Glu Ile Thr Gly Val Tyr Cys Lys Asn Ser
                725                 730                 735

Met Leu His Tyr Ala Glu Tyr Arg Asn Ile Phe Pro Leu Trp Ala Leu
                740                 745                 750

Gly Glu Tyr Arg Lys Arg Val Trp Leu Pro Lys His Gln Gln Leu Lys
            755                 760                 765

Ile

<210> SEQ ID NO 30
<211> LENGTH: 2310
<212> TYPE: DNA
<213> ORGANISM: Panax ginseng

<400> SEQUENCE: 30
atgtggaagc tgaaggttgc tcaaggaaat gatccatatt tgtatagcac taacaacttt    60

```
gttggcagac aatattggga gtttcagccc gatgctggta ctccagaaga gagggaagag    120
gttgaaaaag cacgcaagga ttatgtaaac aataagaagc tacatggaat tcatccatgc    180
agtgatatgc tgatgcgcag gcagcttatt aaagaaagtg gaatcgatct cctaagcata    240
ccgccggtga gattagatga aaacgaacaa gtgaactacg atgcagttac aaccgctgtg    300
aagaaagctc ttcgattgaa ccgggcaatt caagcacacg atggtcactg ccagctgaa     360
aatgcaggct ctttacttta tacacctccc cttatcattg ccctatatat cagcggaacg    420
attgacacta ttctgacaaa acaacacaag aaggaactga ttcgcttcgt ttacaaccat    480
caaaatgagg atggtggatg gggatcctat attgaggggc acagcacgat gattgggtca    540
gtacttagct acgtgatgtt acgtttgcta ggagaaggat tagctgaatc tgatgatgga    600
aatggtgcag ttgagagagg ccggaagtgg atacttgatc atggaggtgc agccagcata    660
ccctcttggg gaaagactta tctagcggtg cttggagtat atgagtggga agggtgcaac    720
ccgctgcccc cagaattctg cttttcct tcaagttttc cttttcatcc agcaaaaatg      780
tggatctact gccggtgcac ttacatgcca atgtcgtatt tgtatgggaa gagatatcat    840
ggaccaataa ccgatcttgt tttatctttg aggcaagaaa tttacaacat tccttatgag    900
cagataaagt ggaatcaaca cgccataac tgttgcaagg aggatctcta ctaccctcat      960
acccttgtac aagacctggt ttgggatggt cttcactact ttagtgaacc attcctcaaa    1020
cgttggccct caacaaact gcgaaaaaga ggtctaaaaa gagttgttga actaatgcgc      1080
tatggtgcca ccgagaccag attcataacc acaggaaatg gggaaaaagc tttacaaata    1140
atgagttggt gggcagaaga tcccaatggt gatgagttta acatcacct tgctagaatt      1200
cctgatttct tatggattgc tgaggatgga atgacagtac agagttttgg tagtcaacta    1260
tgggactgta ttcttgctac tcaagcaatt atcgccacca atatggttga agaatacgga    1320
gattctctta agaaggcgca tttcttcatc aaagaatcgc agataaaaga aaatccaaga    1380
ggagacttcc taaaaatgtg tcgacagttt accaaaggtg cgtggacttt ctctgatcaa    1440
gatcatggtt gcgttgtctc ggactgcaca gctgaagcac taaagtgcct actgttactt    1500
tcacaaatgc cacaggatat tgtcggagaa aaacctgagg ttgagcgatt atatgaggct    1560
gtgaatgttc ttctctattt gcagagtcgt gtaagtggtg gtttcgcagt ttgggagcct    1620
ccagttccaa aaccatattt ggagatgttg aatccttcag aaattttgc agacattgtt      1680
gttgagagag agcacattga atgcactgca tctgtaatca aaggtctgat ggcatttaaa    1740
tgcttgcatc ctgggcatcg tcagaaagag atagaggatt ctgtggcgaa agccatccga    1800
tatcttgaaa gaaaccaaat gcctgatggt tcatggtatg cttttggggg aatttgttc      1860
ctctatggga cattttttac cctatcaggg tttgcttctg ctgggaggac ttatgacaac    1920
agtgaagcag ttcgtaaggg tgttaaattt tcctttcaa cacaaaatga agaaggtggt      1980
tgggggggaga gtcttgaatc atgcccaagc gaaaaattta caccactcaa gggaaacaga    2040
acaaatctag tacaaacatc atgggctatg ttaggtctta tgtttggtgg acaggccgag    2100
agagatccga cacctctgca tagagcagca agttgttga tcaatgcgca aatggacaat      2160
ggagatttcc ctcaacagga aattactgga gtatactgta aaaatagtat gttacattat    2220
gcggagtaca gaaatatatt tcctctttgg gcactcggag aatatcggaa acgtgtttgg    2280
ttgcctaagc accagcagct caaaattta                                       2310
```

<210> SEQ ID NO 31
<211> LENGTH: 2310

```
<212> TYPE: DNA
<213> ORGANIZM: Artificial Sequence
<220> FEATURE:
<223> OTHER INFORMATION: panax ginseng dammarenediol-synthase_E.coli
      codon optimization

<400> SEQUENCE: 31
atgtggaaac agaagggtgc ccaaggaaat gacccatatc tgtatagcac gaacaacttt      60
gttggcagac aatattggga gttccagccc gacgccggta ctccggaaga cgggaagag     120
gttgaaaaag cgcgcaagga ttatgtaaac aataaaaagt tacatggcat tcatccatgc     180
agtgatatgc tgatgcgcag gcagttaatt aaagaatccg gaatcgattt actaagcata     240
ccgccgctga gattagatga aaacgagcag gtgaactacg acgcagtaac aaccgctgtg     300
aagaaagctc ttcgattgaa ccgggctatt caggcacacg atggtcactg gccggctgaa     360
aatgcaggct ctttattata tacacctccc cttatcattg ccctgtatat cagcggcacg     420
attgacacta ttctgacaaa acaacacaag aaggaactga ttcgcttcgt ttacaatcat     480
cagaatgagg atggtggatg ggggagctat attgaggggc acagcacgat gattgggtca     540
gtacttagct acgtgatgtt acgcttgcta ggagaaggct agccgaatc tgatgatgga     600
aatggcgctg tcgaacgcgg ccggaaatgg atactggatc atgggggtgc agccggcata     660
ccctcctggg aaagactta tctagcggtg ttgggagtct atgaatggga aggctgcaac     720
ccgctgcccc cagagttttg gctgtttcct tcaagttttc cttttcatcc agcaaaaatg     780
tggatctact gtcggtgtac gtacatgcca atgtcgtatc tgtatggcaa gagatatcat     840
ggaccaataa ccgatcttgt attatctttg cgccaagaga tttacaatat cccttatgaa     900
cagataaagt ggaaccagca gcgccataac tgttgcaaag aagatctcta ctatcctcat     960
accctttgtac aggatctggt ttgggatggt ctccactact tttccgagcc gttcctcaag    1020
cgttggccct tcaacaaact gcgcaagaga ggtctaaaaa gagttgttga actgatgcgc    1080
tacggtgcta ccgagaccag attcataacc acaggcaatg gggaaaaagc tctgcaaata    1140
atgagctggt gggcggaaga tcccaatggt gacgaattta acaccaccct cgccagaatc    1200
cctgatttc tatggatcgc tgaggacgga atgacagtac agagttttgg cagtcaacta    1260
tgggattgta ttcttgctac tcaagcaatt attgccacca atatggttga agaatacgga    1320
gattctctta agaaagccca cttcttcatc aaagaatcgc agatcaaaga aaatccacgt    1380
ggagacttcc tgaaaatgtg ccgacagttt accaaaggcg cgtggacttt ctccgatcaa    1440
gaccatggtt gtgttgtctc ggactgcacg gctgaagcgc taaagtgtct actgttactt    1500
tcgcaaatgc acaggatat cgtcggggaa aaacctgagg ttgagcgatt atatgaggcc    1560
gtgaatgttc tactctattt gcagagtcgt gtgagtggtg gtttcgcagt gtgggagcct    1620
ccagtcccaa agccatattt ggagatgctg aatccgtcag aaatttttgc agacattgtt    1680
gttgagagag agcatattga atgcactgca tctgtaatca aggtctgat ggcgtttaag    1740
tgcctgcatc ctgggcatcg tcagaaagag atagaggatt ctgtggcgaa agccatccgt    1800
taccttgaaa gaaaccagat gcctgatggt tcatggtatg cttttgggg catttgtttc    1860
ctctatggga catttttttac cctatctggg tttgcatctg ctggacggac ttatgacaac    1920
agtgaagccg ttcgtaaagg tgttaaattt tttcttttcaa cgcagaatga ggagggtggt    1980
tgggggggagt ccctggaatc atgcccgagc gaaaaattta caccgctcaa ggggaaccgc    2040
accaacctag tgcaaacatc atgggcgatg ttggtcttat gtttggcgg tcaggccgag    2100
agagatccga caccgctgca tagagcagcg aagttgttga ttaacgcgca aatggataat    2160
```

```
ggggatttcc ctcaacagga aattacgggc gtgtactgta aaaatagtat gttacattat    2220
gcggagtata gaaatatctt tccgttatgg gcactgggcg aataccggaa acgtgtttgg    2280
ttgccgaagc accagcagct gaaaatttaa                                     2310
```

<210> SEQ ID NO 32
<211> LENGTH: 525
<212> TYPE: PRT
<213> ORGANISM: Artificial Sequence
<220> FEATURE:
<223> OTHER INFORMATION: Truncated HMG-CoA reductase

<400> SEQUENCE: 32

```
Met Asp Gln Leu Val Lys Thr Glu Val Thr Lys Lys Ser Phe Thr Ala
1               5                   10                  15

Pro Val Gln Lys Ala Ser Thr Pro Val Leu Thr Asn Lys Thr Val Ile
            20                  25                  30

Ser Gly Ser Lys Val Lys Ser Leu Ser Ser Ala Gln Ser Ser Ser Ser
        35                  40                  45

Gly Pro Ser Ser Ser Ser Glu Glu Asp Asp Ser Arg Asp Ile Glu Ser
    50                  55                  60

Leu Asp Lys Lys Ile Arg Pro Leu Glu Glu Leu Glu Ala Leu Leu Ser
65                  70                  75                  80

Ser Gly Asn Thr Lys Gln Leu Lys Asn Lys Glu Val Ala Ala Leu Val
                85                  90                  95

Ile His Gly Lys Leu Pro Leu Tyr Ala Leu Glu Lys Lys Leu Gly Asp
            100                 105                 110

Thr Thr Arg Ala Val Ala Val Arg Arg Lys Ala Leu Ser Ile Leu Ala
        115                 120                 125

Glu Ala Pro Val Leu Ala Ser Asp Arg Leu Pro Tyr Lys Asn Tyr Asp
    130                 135                 140

Tyr Asp Arg Val Phe Gly Ala Cys Cys Glu Asn Val Ile Gly Tyr Met
145                 150                 155                 160

Pro Leu Pro Val Gly Val Ile Gly Pro Leu Val Ile Asp Gly Thr Ser
                165                 170                 175

Tyr His Ile Pro Met Ala Thr Thr Glu Gly Cys Leu Val Ala Ser Ala
            180                 185                 190

Met Arg Gly Cys Lys Ala Ile Asn Ala Gly Gly Gly Ala Thr Thr Val
        195                 200                 205

Leu Thr Lys Asp Gly Met Thr Arg Gly Pro Val Val Arg Phe Pro Thr
    210                 215                 220

Leu Lys Arg Ser Gly Ala Cys Lys Ile Trp Leu Asp Ser Glu Glu Gly
225                 230                 235                 240

Gln Asn Ala Ile Lys Lys Ala Phe Asn Ser Thr Ser Arg Phe Ala Arg
                245                 250                 255

Leu Gln His Ile Gln Thr Cys Leu Ala Gly Asp Leu Leu Phe Met Arg
            260                 265                 270

Phe Arg Thr Thr Thr Gly Asp Ala Met Gly Met Asn Met Ile Ser Lys
        275                 280                 285

Gly Val Glu Tyr Ser Leu Lys Gln Met Val Glu Tyr Gly Trp Glu
    290                 295                 300

Asp Met Glu Val Val Ser Val Ser Gly Asn Tyr Cys Thr Asp Lys Lys
305                 310                 315                 320

Pro Ala Ala Ile Asn Trp Ile Glu Gly Arg Gly Lys Ser Val Val Ala
                325                 330                 335
```

```
Glu Ala Thr Ile Pro Gly Asp Val Val Arg Lys Val Leu Lys Ser Asp
            340                 345                 350
Val Ser Ala Leu Val Glu Leu Asn Ile Ala Lys Asn Leu Val Gly Ser
        355                 360                 365
Ala Met Ala Gly Ser Val Gly Gly Phe Asn Ala His Ala Ala Asn Leu
    370                 375                 380
Val Thr Ala Val Phe Leu Ala Leu Gly Gln Asp Pro Ala Gln Asn Val
385                 390                 395                 400
Glu Ser Ser Asn Cys Ile Thr Leu Met Lys Glu Val Asp Gly Asp Leu
                405                 410                 415
Arg Ile Ser Val Ser Met Pro Ser Ile Glu Val Gly Thr Ile Gly Gly
            420                 425                 430
Gly Thr Val Leu Glu Pro Gln Gly Ala Met Leu Asp Leu Leu Gly Val
        435                 440                 445
Arg Gly Pro His Ala Thr Ala Pro Gly Thr Asn Ala Arg Gln Leu Ala
    450                 455                 460
Arg Ile Val Ala Cys Ala Val Leu Ala Gly Glu Leu Ser Leu Cys Ala
465                 470                 475                 480
Ala Leu Ala Ala Gly His Leu Val Gln Ser His Met Thr His Asn Arg
                485                 490                 495
Lys Pro Ala Glu Pro Thr Lys Pro Asn Asn Leu Asp Ala Thr Asp Ile
            500                 505                 510
Asn Arg Leu Lys Asp Gly Ser Val Thr Cys Ile Lys Ser
            515                 520                 525

<210> SEQ ID NO 33
<211> LENGTH: 1578
<212> TYPE: DNA
<213> ORGANISM: Artificial Sequence
<220> FEATURE:
<223> OTHER INFORMATION: Truncated HMG-CoA reductase

<400> SEQUENCE: 33
atggaccaat tggtgaaaac tgaagtcacc aagaagtctt ttactgctcc tgtacaaaag      60
gcttctacac cagtttttaac caataaaaca gtcatttctg gatcgaaagt caaaagttta    120
tcatctgcgc aatcgagctc atcaggacct tcatcatcta gtgaggaaga tgattcccgc    180
gatattgaaa gcttggataa gaaaatacgt cctttagaag aattagaagc attattaagt    240
agtggaaata caaaacaatt gaagaacaaa gaggtcgctg ccttggttat tcacggtaag    300
ttacctttgt acgctttgga gaaaaaatta ggtgatacta cgagagcggt tgcggtacgt    360
aggaaggctc tttcaatttt ggcagaagct cctgtattag catctgatcg tttaccatat    420
aaaaattatg actacgaccg cgtatttggc gcttgttgtg aaaatgttat aggttacatg    480
cctttgcccg ttggtgttat aggccccttg gttatcgatg gtacatctta tcatatacca    540
atggcaacta cagagggttg tttggtagct tctgccatgc gtggctgtaa ggcaatcaat    600
gctggcggtg gtgcaacaac tgtttttaact aaggatggta tgacaagagg cccagtagtc    660
cgtttcccaa ctttgaaaag atctggtgcc tgtaagatat ggttagactc agaagaggga    720
caaaacgcaa ttaaaaaagc ttttaactct acatcaagat tgcacgtct gcaacatatt    780 caaacttgtc tagcaggaga tttactcttc atgagattta aacaactac tggtgacgca    840 atgggtatga atatgattt caaggggtgtc gaatactcat taaagcaaat ggtagaagag    900
tatggctggg aagatatgga ggttgtctcc gtttctggta actactgtac cgacaaaaaa    960
```

```
ccagctgcca tcaactggat cgaaggtcgt ggtaagagtg tcgtcgcaga agctactatt   1020
cctggtgatg ttgtcagaaa agtgttaaaa agtgatgttt ccgcattggt tgagttgaac   1080
attgctaaga atttggttgg atctgcaatg gctgggtctg ttggtggatt taacgcacat   1140
gcagctaatt tagtgacagc tgttttcttg gcattaggac aagatcctgc acaaaatgtc   1200
gaaagttcca actgtataac attgatgaaa gaagtggacg gtgatttgag aatttccgta   1260
tccatgccat ccatcgaagt aggtaccatc ggtggtggta ctgttctaga accacaaggt   1320
gccatgttgg acttattagg tgtaagaggc ccacatgcta ccgctcctgg taccaacgca   1380
cgtcaattag caagaatagt tgcctgtgcc gtcttggcag gtgaattatc cttatgtgct   1440
gccctagcag ccggccattt ggttcaaagt catatgaccc acaacaggaa acctgctgaa   1500
ccaacaaaac ctaacaattt ggacgccact gatataaatc gtttgaaaga tgggtccgtc   1560
acctgcatta aatcctaa                                                  1578
```

<210> SEQ ID NO 34
<211> LENGTH: 482
<212> TYPE: PRT
<213> ORGANISM: Panax ginseng

<400> SEQUENCE: 34

```
Met Val Leu Phe Phe Ser Leu Ser Leu Leu Leu Pro Leu Leu Leu
1               5                   10                  15

Leu Phe Ala Tyr Phe Ser Tyr Thr Lys Arg Ile Pro Gln Lys Glu Asn
            20                  25                  30

Asp Ser Lys Ala Pro Leu Pro Pro Gly Gln Thr Gly Trp Pro Leu Ile
        35                  40                  45

Gly Glu Thr Leu Asn Tyr Leu Ser Cys Val Lys Ser Gly Val Ser Glu
    50                  55                  60

Asn Phe Val Lys Tyr Arg Lys Glu Lys Tyr Ser Pro Lys Val Phe Arg
65                  70                  75                  80

Thr Ser Leu Leu Gly Glu Pro Met Ala Ile Leu Cys Gly Pro Glu Gly
                85                  90                  95

Asn Lys Phe Leu Tyr Ser Thr Glu Lys Lys Leu Val Gln Val Trp Phe
            100                 105                 110

Pro Ser Ser Val Glu Lys Met Phe Pro Arg Ser His Gly Glu Ser Asn
        115                 120                 125

Ala Asp Asn Phe Ser Lys Val Arg Gly Lys Met Met Phe Leu Leu Lys
    130                 135                 140

Val Asp Gly Met Lys Lys Tyr Val Gly Leu Met Asp Arg Val Met Lys
145                 150                 155                 160

Gln Phe Leu Glu Thr Asp Trp Asn Arg Gln Gln Ile Asn Val His
                165                 170                 175

Asn Thr Val Lys Lys Tyr Thr Val Thr Met Ser Cys Arg Val Phe Met
            180                 185                 190

Ser Ile Asp Asp Glu Glu Gln Val Thr Arg Leu Gly Ser Ser Ile Gln
        195                 200                 205

Asn Ile Glu Ala Gly Leu Leu Ala Val Pro Ile Asn Ile Pro Gly Thr
    210                 215                 220

Ala Met Asn Arg Ala Ile Lys Thr Val Lys Leu Leu Thr Arg Glu Val
225                 230                 235                 240

Glu Ala Val Ile Lys Gln Arg Lys Val Asp Leu Leu Glu Asn Lys Gln
                245                 250                 255

Ala Ser Gln Pro Gln Asp Leu Leu Ser His Leu Leu Leu Thr Ala Asn
```

```
                    260                 265                 270
Gln Asp Gly Gln Phe Leu Ser Glu Ser Asp Ile Ala Ser His Leu Ile
            275                 280                 285
Gly Leu Met Gln Gly Gly Tyr Thr Thr Leu Asn Gly Thr Ile Thr Phe
        290                 295                 300
Val Leu Asn Tyr Leu Ala Glu Phe Pro Asp Val Tyr Asn Gln Val Leu
305                 310                 315                 320
Lys Glu Gln Val Glu Ile Ala Asn Ser Lys His Pro Lys Glu Leu Leu
                325                 330                 335
Asn Trp Glu Asp Leu Arg Lys Met Lys Tyr Ser Trp Asn Val Ala Gln
            340                 345                 350
Glu Val Leu Arg Ile Ile Pro Pro Gly Val Gly Thr Phe Arg Glu Ala
        355                 360                 365
Ile Thr Asp Phe Thr Tyr Ala Gly Tyr Leu Ile Pro Lys Gly Trp Lys
        370                 375                 380
Met His Leu Ile Pro His Asp Thr His Lys Asn Pro Thr Tyr Phe Pro
385                 390                 395                 400
Ser Pro Glu Lys Phe Asp Pro Thr Arg Phe Glu Gly Asn Gly Pro Ala
                405                 410                 415
Pro Tyr Thr Phe Thr Pro Phe Gly Gly Gly Pro Arg Met Cys Pro Gly
            420                 425                 430
Ile Glu Tyr Ala Arg Leu Val Ile Leu Ile Phe Met His Asn Val Val
        435                 440                 445
Thr Asn Phe Arg Trp Glu Lys Leu Ile Pro Asn Glu Lys Ile Leu Thr
450                 455                 460
Asp Pro Ile Pro Arg Phe Ala His Gly Leu Pro Ile His Leu His Pro
465                 470                 475                 480
His Asn
```

<210> SEQ ID NO 35
<211> LENGTH: 1449
<212> TYPE: DNA
<213> ORGANISM: Panax ginseng

<400> SEQUENCE: 35

```
atggtgttgt ttttctccct atctcttctt ctccttcccc tattattatt gtttgcctat      60
ttttcttata caaaacgcat cccccagaaa gaaaatgatt caaagctccc ctccccccca     120
ggtcaaacag gttggccttt gataggcgaa actcttaatt atttatcttg tgtcaaaagt     180
gggtttctg aaaattttgt gaaatatagg aaggaaaagt attcccccaa agttttcagg      240
acatcacttt taggagaacc gatggcaatc ttgtgtgggc cggagggcaa caaattcctc     300
tactcaacgg aaaaaaagct agtccaagtt tggttcccga gcagtgttga aaagatgttc     360
cccagatctc atggcgaatc caacgcagac aacttctcca agtacgcgg caaaatgatg      420
tttctactca aggtggacgg gatgaaaaaa tatgttggcc taatggacag ggtgatgaaa     480
cagtttttag agacagattg gaatcgccaa caacagatca acgttcataa cacggttaag     540
aaatacacgg tcacgatgtc gtgtcgggtg tttatgagta tcgatgatga agagcaagtt     600
acaagacttg gcagctcaat tcagaacata gaggccggac tccttgccgt gcctataaat     660
ataccgggga ctgctatgaa tcgtgccatt aagaccgtaa agttgctaac tagagaggtt     720
gaggcggtga ttaagcaaag aaaagtggat cttttggaga ataagcaagc gtcccaaccg     780
caagatttat tgtcacactt gctacttacg gccaatcagg atggccaatt tttgagcgaa     840
```

-continued

```
tcggatattg ctagccactt gataggcttg atgcaaggtg gctataccac cttaaatggt      900
acaatcacct tcgttctcaa ctatcttgca gagtttcctg atgtctacaa tcaagtcctt      960
aaagagcaag tggaaatagc aaactcaaaa cacccaaaag agttgcttaa ttgggaggat     1020
ttgaggaaga tgaagtattc gtggaatgtt gctcaagagg tattgagaat aataccacca     1080
ggagttggaa cattcagaga agctattacc gatttcacct atgctggata tttaattcca     1140
aagggatgga gatgcatct gattccacat gacacgcaca agaacccaac atatttcca      1200 agtccagaaa aattcgatcc aaccaggttt gaaggaaatg gtccggctcc atatacattt     1260
actcctttcg gaggaggacc tcgaatgtgt ccgggaattg agtatgcacg tctagtaata     1320
ctcattttta tgcacaatgt ggttacaaac ttcagatggg agaagctcat ccctaatgaa     1380
aaaattctca ccgatcccat tccaagattt gcgcatggac ttcccattca tctacatccc     1440
cacaattaa                                                             1449
```

<210> SEQ ID NO 36
<211> LENGTH: 712
<212> TYPE: PRT
<213> ORGANISM: Arabidopsis thaliana

<400> SEQUENCE: 36

```
Met Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
            100                 105                 110

Thr Gly Thr Ala Glu Gly Phe Ala Lys Ala Leu Gly Glu Glu Ala Lys
        115                 120                 125

Ala Arg Tyr Glu Lys Thr Arg Phe Lys Ile Val Asp Leu Asp Asp Tyr
    130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
        195                 200                 205

Tyr Glu His Phe Asn Lys Val Ala Lys Val Val Asp Asp Ile Leu Val
    210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Glu Gly Asp Thr Ala Val Ala Thr
```

```
            260                 265                 270
Pro Tyr Thr Ala Ala Val Leu Glu Tyr Arg Val Ser Ile His Asp Ser
            275                 280                 285

Glu Asp Ala Lys Phe Asn Asp Ile Asn Met Ala Asn Gly Asn Gly Tyr
290                 295                 300

Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
            325                 330                 335

Phe Asp Ile Ala Gly Ser Gly Leu Thr Tyr Glu Thr Gly Asp His Val
            340                 345                 350

Gly Val Leu Cys Asp Asn Leu Ser Glu Thr Val Asp Glu Ala Leu Arg
            355                 360                 365

Leu Leu Asp Met Ser Pro Asp Thr Tyr Phe Ser Leu His Ala Glu Lys
            370                 375                 380

Glu Asp Gly Thr Pro Ile Ser Ser Ser Leu Pro Pro Phe Pro Pro
385                 390                 395                 400

Cys Asn Leu Arg Thr Ala Leu Thr Arg Tyr Ala Cys Leu Leu Ser Ser
                405                 410                 415

Pro Lys Lys Ser Ala Leu Val Ala Leu Ala Ala His Ala Ser Asp Pro
            420                 425                 430

Thr Glu Ala Glu Arg Leu Lys His Leu Ala Ser Pro Ala Gly Lys Val
            435                 440                 445

Asp Glu Tyr Ser Lys Trp Val Val Glu Ser Gln Arg Ser Leu Leu Glu
450                 455                 460

Val Met Ala Glu Phe Pro Ser Ala Lys Pro Pro Leu Gly Val Phe Phe
465                 470                 475                 480

Ala Gly Val Ala Pro Arg Leu Gln Pro Arg Phe Tyr Ser Ile Ser Ser
                485                 490                 495

Ser Pro Lys Ile Ala Glu Thr Arg Ile His Val Thr Cys Ala Leu Val
            500                 505                 510

Tyr Glu Lys Met Pro Thr Gly Arg Ile His Lys Gly Val Cys Ser Thr
            515                 520                 525

Trp Met Lys Asn Ala Val Pro Tyr Glu Lys Ser Glu Asn Cys Ser Ser
            530                 535                 540

Ala Pro Ile Phe Val Arg Gln Ser Asn Phe Lys Leu Pro Ser Asp Ser
545                 550                 555                 560

Lys Val Pro Ile Ile Met Ile Gly Pro Gly Thr Gly Leu Ala Pro Phe
                565                 570                 575

Arg Gly Phe Leu Gln Glu Arg Leu Ala Leu Val Glu Ser Gly Val Glu
            580                 585                 590

Leu Gly Pro Ser Val Leu Phe Phe Gly Cys Arg Asn Arg Arg Met Asp
            595                 600                 605

Phe Ile Tyr Glu Glu Glu Leu Gln Arg Phe Val Glu Ser Gly Ala Leu
            610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                645                 650                 655

Ser Gln Gly Ala Tyr Leu Tyr Val Cys Gly Asp Ala Lys Gly Met Ala
                660                 665                 670

Arg Asp Val His Arg Ser Leu His Thr Ile Ala Gln Glu Gln Gly Ser
            675                 680                 685
```

Met Asp Ser Thr Lys Ala Glu Gly Phe Val Lys Asn Leu Gln Thr Ser
690 695 700

Gly Arg Tyr Leu Arg Asp Val Trp
705 710

<210> SEQ ID NO 37
<211> LENGTH: 2139
<212> TYPE: DNA
<213> ORGANISM: Arabidopsis thaliana

<400> SEQUENCE: 37

| | | | |
|---|---|---|---|
| atgtcctctt cttcttcttc gtcaacctcc atgatcgatc tcatggcagc aatcatcaaa | | | 60 |
| ggagagcctg taattgtctc cgacccagct aatgcctccg cttacgagtc cgtagctgct | | | 120 |
| gaattatcct ctatgcttat agagaatcgt caattcgcca tgattgttac cacttccatt | | | 180 |
| gctgttctta ttggttgcat cgttatgctc gtttggagga gatccggttc tgggaattca | | | 240 |
| aaacgtgtcg agcctcttaa gcctttggtt attaagcctc gtgaggaaga gattgatgat | | | 300 |
| gggcgtaaga aagttaccat cttttttcggt acacaaactg gtactgctga aggttttgca | | | 360 |
| aaggctttag gagaagaagc taaagcaaga tatgaaaaga ccagattcaa aatcgttgat | | | 420 |
| ttggatgatt acgcggctga tgatgatgag tatgaggaga aattgaagaa agaggatgtg | | | 480 |
| gctttcttct tcttagccac atatggagat ggtgagccta ccgacaatgc agcgagattc | | | 540 |
| tacaaatggt tcaccgaggg aatgacaga ggagaatggc ttaagaactt gaagtatgga | | | 600 |
| gtgtttggat taggaaacag acaatatgag cattttaata aggttgccaa agttgtagat | | | 660 |
| gacattcttg tcgaacaagg tgcacagcgt cttgtacaag ttggtcttgg agatgatgac | | | 720 |
| cagtgtattg aagatgactt taccgcttgg cgagaagcat gtggcccga gcttgataca | | | 780 |
| atactgaggg aagaagggga tacagctgtt gccacaccat acactgcagc tgtgttagaa | | | 840 |
| tacagagttt ctattcacga ctctgaagat gccaaattca atgatataaa catggcaaat | | | 900 |
| gggaatggtt acactgtgtt tgatgctcaa catccttaca agcaaatgt cgctgttaaa | | | 960 |
| agggagcttc atactcccga gtctgatcgt tcttgtatcc atttggaatt tgacattgct | | | 1020 |
| ggaagtggac ttacgtatga aactggagat catgttggtg tactttgtga aacttaagt | | | 1080 |
| gaaactgtag atgaagctct tagattgctg gatatgtcac ctgatactta tttctcactt | | | 1140 |
| cacgctgaaa agaagacgg cacaccaatc agcagctcac tgcctcctcc cttcccacct | | | 1200 |
| tgcaacttga aacagcgct tacacgatat gcatgtcttt tgagttctcc aaagaagtct | | | 1260 |
| gctttagttg cgttggctgc tcatgcatct gatcctaccg aagcagaacg attaaaacac | | | 1320 |
| cttgcttcac ctgctggaaa ggttgatgaa tattcaaagt gggtagtaga gagtcaaaga | | | 1380 |
| agtctacttg aggtgatggc cgagtttcct tcagccaagc caccttgg tgtcttcttc | | | 1440 |
| gctggagttg ctccaaggtt gcagcctagg ttctattcga tatcatcatc gcccaagatt | | | 1500 |
| gctgaaacta gaattcacgt cacatgtgca ctggtttatg agaaaatgcc aactggcagg | | | 1560 |
| attcataagg gagtgtgttc cacttggatg aagaatgctg tgccttacga aagagtgaa | | | 1620 |
| aactgttcct cggcgccgat atttgttagg caatccaact tcaagcttcc ttctgattct | | | 1680 |
| aaggtaccga tcatcatgat cggtccaggg actggattag ctccattcag aggattcctt | | | 1740 |
| caggaaagac tagcgttggt agaatctggt gttgaacttg gccatcagt tttgttcttt | | | 1800 |
| ggatgcagaa accgtagaat ggattttcatc tacgaggaag agctccagcg atttgttgag | | | 1860 |
| agtggtgctc tcgcagagct aagtgtcgcc ttctctcgtg aaggacccac caaagaatac | | | 1920 |

```
gtacagcaca agatgatgga caaggcttct gatatctgga atatgatctc tcaaggagct    1980
tatttatatg tttgtggtga cgccaaaggc atggcaagag atgttcacag atctctccac    2040
acaatagctc aagaacaggg gtcaatggat tcaactaaag cagagggctt cgtgaagaat    2100
ctgcaaacga gtggaagata tcttagagat gtatggtaa                           2139
```

<210> SEQ ID NO 38
<211> LENGTH: 2139
<212> TYPE: DNA
<213> ORGANISM: Artificial Sequence
<220> FEATURE:
<223> OTHER INFORMATION: Arabidopsis thaliana cytochrome p450
      reductase_E.coli codon optimization

<400> SEQUENCE: 38

```
atgtcctctt cttcttcttc gtcaaccagc atgattgatc tcatggcagc aatcatcaaa     60
ggggaacctg taattgtcag cgacccagct aatgcctccg cttatgagtc cgtagctgcg    120
gaactgtcca gtatgcttat agagaatcgt caattcgcca tgattgttac cacttccatt    180
gctgttctta ttggttgcat cgtgatgctc gtttggcgga gatccggttc tggaaatagt    240
aaacgtgtcg agcctcttaa gcctttggtg attaaacctc gtgaggaaga gattgatgat    300
ggtcgtaaga agttaccat cttttttcggt acacagacgg ggacggcgga aggttttgca    360
aaggctttag gtgaggaagc taaagcacgt tatgaaaaga ccagatttaa gatcgtagat    420
ttagatgatt acgcggcgga tgatgacgag tatgaggaaa aacttaaaaa gaagatgtg    480 gcttttttct tcttagccac atacggggac ggtgagccca cgacaatgc agcacggttc    540 tacaaatggt tcacggaggg gaatgacaga ggagaatggc ttaagaactt gaagtatggt    600
gtgtttggat taggaaaccg ccagtatgag cattttaata aggttgccaa agtcgtagat    660
gacattcttg tagaacaagg tgcacagcgt cttgtacagg tgggtcttgg agatgacgat    720
cagtgtattg aggatgactt taccgcgtgg cgtgaggcat tgtggcccga acttgataca    780
atcctgaggg aagaaggcga cacggcggtc gccacaccat ataccgcagc ggtgctggaa    840
taccgagttt ctattcacga cagcgaagac gccaaattca atgatataaa catggcaaat    900
gggaacggtt acactgtgtt tgatgctcaa catccttata agcaaatgt cgctgtgaaa    960 cgcgaacttc atactcccga gtctgatcgt tcttgcatcc atttggagtt tgacattgct   1020
ggcagtgggc ttacgtatga aactggagat catgttgggg tactctgtga acttaagt   1080 gaaaccgtgg atgaagctct tcgcttgctg gatatgtcac ctgacactta cttctcactc   1140
cacgctgaga agaagacgg cacaccaatc agcagctcac tgcctcctcc cttccctcct   1200
tgcaacctca gaaccgcgct tacacgatat gcatgtcttt tgagttctcc taaaaaatct   1260
gctttagttg cgttggccgc tcatgcatct gatcctaccg aagcagaacg attaaagcac   1320
cttgcttcac ctgctggcaa ggttgacgaa tattcaaagt gggtagttga agtcaaaga   1380 agtctacttg aagtgatggc cgaatttcct tcagccaagc caccgctggg tgtcttcttc   1440
gctggagttg cgccaaggtt gcagcctcgg ttctattcga tatcatcatc gcccaagatt   1500
gccgaaaccc ggattcacgt cacatgtgca ctggtttatg aaaaaatgcc aacgggcagg   1560
attcacaagg gtgtgtgttc cacgtggatg aagaatgcgg tgccttacga gaagagtgaa   1620
aactgctcct cggcgccgat atttgttcgc cagtcgaact tcaaattgcc gtctgattct   1680
aaagtaccga taatcatgat cggtccaggc actggcttag ctccgtttag aggattttta   1740
caggaaagac tagccttggt ggaatctggc gttgagcttg gccatcagt tttgttttt   1800
```

```
ggatgcagaa accgtagaat ggatttcatc tacgaggaag agttacagcg ttttgtcgag   1860
agtggtgctc tggctgagct aagcgtcgcc ttctctcgtg aaggcccgac caaagaatac   1920
gtacagcaca agatgatgga caaggcctct gatatctgga atatgatcag ccagggtgcc   1980
tatttatatg tttgtggtga cgcgaaaggc atggcaagag atgttcatcg gtctctccac   2040
acaatagctc aagaacaggg ctcaatggat tcgactaaag cagaggggtt cgtgaagaat   2100
ctgcaaacga gtgggagata tcttagagac gtgtggtaa                         2139
```

<210> SEQ ID NO 39
<211> LENGTH: 469
<212> TYPE: PRT
<213> ORGANISM: Panax ginseng

<400> SEQUENCE: 39

```
Met Asp Leu Phe Ile Ser Ser Gln Leu Leu Leu Leu Val Phe Cys
1               5                   10                  15

Leu Phe Leu Phe Trp Asn Phe Lys Pro Ser Ser Gln Asn Lys Leu Pro
            20                  25                  30

Pro Gly Lys Thr Gly Trp Pro Ile Ile Gly Glu Thr Leu Glu Phe Ile
        35                  40                  45

Ser Cys Gly Gln Lys Gly Asn Pro Glu Lys Phe Val Thr Gln Arg Met
    50                  55                  60

Asn Lys Tyr Ser Pro Asp Val Phe Thr Thr Ser Leu Ala Gly Glu Lys
65                  70                  75                  80

Met Val Val Phe Cys Gly Ala Ser Gly Asn Lys Phe Ile Phe Ser Asn
                85                  90                  95

Glu Asn Lys Leu Val Val Ser Trp Trp Pro Pro Ala Ile Ser Lys Ile
            100                 105                 110

Leu Thr Ala Thr Ile Pro Ser Val Glu Lys Ser Lys Ala Leu Arg Ser
        115                 120                 125

Leu Ile Val Glu Phe Leu Lys Pro Glu Ala Leu His Lys Phe Ile Ser
    130                 135                 140

Val Met Asp Arg Thr Thr Arg Gln His Phe Glu Asp Lys Trp Asn Gly
145                 150                 155                 160

Ser Thr Glu Val Lys Ala Phe Ala Met Ser Glu Ser Leu Thr Phe Glu
                165                 170                 175

Leu Ala Cys Trp Leu Leu Phe Ser Ile Asn Asp Pro Val Gln Val Gln
            180                 185                 190

Lys Leu Ser His Leu Phe Glu Lys Val Lys Ala Gly Leu Leu Ser Leu
        195                 200                 205

Pro Leu Asn Phe Pro Gly Thr Ala Phe Asn Arg Gly Ile Lys Ala Ala
    210                 215                 220

Asn Leu Ile Arg Lys Glu Leu Ser Val Val Ile Lys Gln Arg Arg Ser
225                 230                 235                 240

Asp Lys Leu Gln Thr Arg Lys Asp Leu Leu Ser His Val Met Leu Ser
                245                 250                 255

Asn Gly Glu Gly Glu Lys Phe Phe Ser Glu Met Asp Ile Ala Asp Val
            260                 265                 270

Val Leu Asn Leu Leu Ile Ala Ser His Asp Thr Thr Ser Ser Ala Met
        275                 280                 285

Gly Ser Val Val Tyr Phe Leu Ala Asp His Pro His Ile Tyr Ala Lys
    290                 295                 300

Val Leu Thr Glu Gln Met Glu Ile Ala Lys Ser Lys Gly Ala Glu Glu
305                 310                 315                 320
```

Leu Leu Ser Trp Glu Asp Ile Lys Arg Met Lys Tyr Ser Arg Asn Val
            325                 330                 335

Ile Asn Glu Ala Met Arg Leu Val Pro Pro Ser Gln Gly Gly Phe Lys
        340                 345                 350

Val Val Thr Ser Lys Phe Ser Tyr Ala Asn Phe Ile Ile Pro Lys Gly
            355                 360                 365

Trp Lys Ile Phe Trp Ser Val Tyr Ser Thr His Lys Asp Pro Lys Tyr
    370                 375                 380

Phe Lys Asn Pro Glu Glu Phe Asp Pro Ser Arg Phe Glu Gly Asp Gly
385                 390                 395                 400

Pro Met Pro Phe Thr Phe Ile Pro Phe Gly Gly Pro Arg Met Cys
                405                 410                 415

Pro Gly Ser Glu Phe Ala Arg Leu Glu Val Leu Ile Phe Met His His
            420                 425                 430

Leu Val Thr Asn Phe Lys Trp Glu Lys Val Phe Pro Asn Glu Lys Ile
            435                 440                 445

Ile Tyr Thr Pro Phe Pro Phe Pro Glu Asn Gly Leu Pro Ile Arg Leu
    450                 455                 460

Ser Pro Cys Thr Leu
465

<210> SEQ ID NO 40
<211> LENGTH: 1410
<212> TYPE: DNA
<213> ORGANISM: Panax ginseng

<400> SEQUENCE: 40
atggatctct ttatctcatc tcaactactt cttctactag tcttttgctt attcctcttt     60
tggaatttca aaccaagtag ccaaaacaaa ctgcctccgg gcaaacagg atggcccata    120 attggagaaa cactagaatt catctcctgt ggccaaaaag caaccctga aaagttcgta     180 acacaaagaa tgaacaaata ctcccctgat gtcttcacaa catccttagc aggcgagaaa    240
atggtagttt tctgcggtgc ctcggggaac aaattcattt tctccaacga aaacaagctt    300
gttgtgtcct ggtggccccc tgccatatcc aaaatcctaa ctgcaacaat accttcggta    360
gagaaaagca aagccttgcg gagtctaatt gttgaattct aaaacccga gcgctccac     420 aagtttattt ctgtcatgga tcggacaacg aggcagcact tgaagacaa tggaacggg     480 agtacagaag tgaaagcttt cgctatgtca gagtcgctga cttttgagtt ggcctgttgg    540
ctgctcttta gcataaatga tccggtgcag gtgcagaagc tttctcatct ttttgagaag    600
gttaaagcgg gattattgtc tttacctttta aatttcccgg gcacggcttt taaccgtggg    660
atcaaggccg ccaatcttat tagaaaagag ctttcggtgg tgataaaaca gaggagaagt    720
gataaattac agactcgaaa ggatcttttg tcccacgtta tgcttttccaa tggcgagggc    780 gagaaatttt tcagcgaaat ggatattgcg gacgttgttc ttaatttact gattgctagc    840
catgatacca ctagcagtgc catgggctct gtggtctact tcttgcaga tcatcctcac     900 atctatgcta aagttctcac agaacaaatg gagatcgcaa agtcgaaagg ggcagaagaa    960
cttttgagct gggaggacat aaagaggatg aagtattccc gcaatgttat aaatgaagct    1020
atgagattag tacctccttc tcaaggaggt tttaaagtag ttacaagtaa attcagttac   1080

```
gcaaacttca tcattcccaa aggatggaag atctttttgga gcgtatactc gacacataaa    1140
gatcccaaat actttaaaaa tccagaggag tttgatcctt caagatttga aggagatgga    1200
cctatgccat tcacatttat accatttgga ggaggaccaa ggatgtgccc tgggagtgag    1260
tttgctcgtc tggaggtact aatattcatg caccatttgg ttaccaattt taagtgggag    1320
aaggtgtttc ccaatgaaaa gattatttat actccatttc ccttcccgga gaatggtctt    1380
cctattcgtc tatcaccttg tacgctttaa                                     1410
```

<210> SEQ ID NO 41
<211> LENGTH: 1410
<212> TYPE: DNA
<213> ORGANISM: Artificial Sequence
<220> FEATURE:
<223> OTHER INFORMATION: Panax ginseng protopanaxatriol synthase_yeast codon optimization

<400> SEQUENCE: 41

```
atggacctct ttatctcttc tcaactactt cttttgttgg tcttttgctt gttcctattc     60
tggaacttca aaccatcaag ccaaaataaa ttacctccgg caaaaccgg atggccaata    120 attggagaaa ccctagaatt tatctcatgt ggccaaaaag gaaccccga aaagttcgta    180 actcaaagaa tgaacaaata ttcacctgat gtctttacaa catccttagc aggtgagaag    240
atggtagttt tctgtggtgc ctcgggtaac aagtttattt tctccaacga aaacaaactt    300
gttgtgtcct ggtggccccc tgccatctcc aaaattctaa ctgcaacaat accttcggtc    360
gagaaatcca aggccttgcg tagtctgata gttgaatttt taaaacccga ggcgctccat    420
aagtttattt ctgttatgga tagaactacg aggcaacatt ttgaagacaa atggaacgga    480
agtacagagg ttaaggcttt cgctatgtca gaatcgctga cttttgagtt ggcctgttgg    540
ctattattca gcataaatga cccggtacag gtgcagaagt tgtctcattt atttgaaaag    600
gttaaagcgg gattattgtc tttacctctt aattttccag gtacggcttt caaccgtggg    660
atcaaggctg caaatcttat tagaaaagaa ctttcggtgg tgataaaaca aagaagaagt    720
gataaattac agactcgaaa ggatcttttg tcccacgtca tgctttctaa cggtgaaggc    780
gaaaagtttt tcagtgaaat ggatattgcg gacgttgttc ttaatttact cattgcttct    840
catgatacca cttctagtgc catgggctct gtggtctact tcttgcaga tcatcctcac    900 atttatgcta aagttttaac ggaacaaatg gagatcgcaa agtcaaaggg ggcagaagaa    960
cttttgagct gggaggacat aaagaggatg aagtattccc gcaatgttat aaatgaagct   1020
atgagattag tacctccatc tcaaggaggt tttaaagttg tgacaagtaa attcagttat   1080
gctaatttca tcattcccaa aggttggaaa atcttttgga gcgtatactc tacccataaa   1140
gatccaaaat actttaaaaa tccagaagaa tttgatcctt caagatttga aggagatgga   1200
ccaatgccat ttacatttat accatttggt ggcggaccaa ggatgtgccc tggctcagag   1260
tttgctagac tggaggtact aatttttcatg caccatttgg ttaccaattt taagtgggaa   1320
aaagtcttcc caaatgaaaa gattatctat actccattcc ccttcccgga gaatggtctt   1380
cctattagac tatcaccttg tactttataa                                    1410
```